United States Patent [19]
Staniforth et al.

[11] Patent Number: 6,106,865
[45] Date of Patent: *Aug. 22, 2000

[54] PHARMACEUTICAL EXCIPIENT HAVING IMPROVED COMPRESSIBILITY

[75] Inventors: John N. Staniforth, Bath, United Kingdom; Edward A. Hunter, Glenham; Bob E. Sherwood, Amenia, both of N.Y.

[73] Assignee: Edward Mendell Co., Inc., Patterson, N.Y.

[*] Notice: This patent is subject to a terminal disclaimer.

[21] Appl. No.: 09/037,841

[22] Filed: Mar. 10, 1998

Related U.S. Application Data

[63] Continuation-in-part of application No. 08/660,553, Jun. 10, 1996, Pat. No. 5,866,166, application No. 08/486,183, Jun. 7, 1995, Pat. No. 5,725,883, application No. 08/724,613, Sep. 30, 1996, Pat. No. 5,725,884, which is a continuation of application No. 08/370,576, Jan. 9, 1995, Pat. No. 5,585,115.

[51] Int. Cl.⁷ .................................................. A61K 9/14
[52] U.S. Cl. .......................... 424/489; 424/480; 424/458; 424/494; 424/464; 424/495; 424/496; 424/497; 424/49; 106/154.51
[58] Field of Search .................................... 424/489, 480, 424/458, 494–497, 464; 106/154.51

[56] References Cited

U.S. PATENT DOCUMENTS

| | | | |
|---|---|---|---|
| 4,810,516 | 3/1989 | Kong-Chan | 426/548 |
| 5,725,884 | 3/1998 | Sherwood et al. | 424/489 |
| 5,733,578 | 3/1998 | Hunter et al. | 424/489 |
| 5,858,409 | 1/1999 | Karetney et al. | 424/489 |
| 5,858,412 | 1/1999 | Staniforth et al. | 424/489 |
| 5,866,166 | 2/1999 | Staniforth et al. | 424/489 |

FOREIGN PATENT DOCUMENTS 0167191  1/1986  European Pat. Off. ....... A61K 33/02

*Primary Examiner*—Thurman K. Page
*Assistant Examiner*—William E. Benston, Jr.
*Attorney, Agent, or Firm*—Davidson Davidson & Kappel, LLC

[57] ABSTRACT

A composition, comprising (a) microcrystalline cellulose; and (b) a compressibility augmenting agent which (i) physically restricts the proximity of the interface between adjacent cellulose surfaces; or (ii) inhibits interactions between adjacent cellulose surfaces; or (iii) accomplishes both (i) and (ii) above, is disclosed. The composition is in the form of agglomerated particles of microcrystalline cellulose and the compressibility augmenting agent in intimate association with each other.

33 Claims, 9 Drawing Sheets

PHARMACEUTICAL EXCIPIENT HAVING IMPROVED COMPRESSIBILITY

BACKGROUND OF THE INVENTION

This is a continuation-in-part of U.S. application Ser. No. 08/660,553 filed Jun. 10, 1996, now U.S. Pat. No. 5,866,166 U.S. application Ser. No. 08/486,183, filed Jun. 7, 1995 now U.S. Pat. No. 5,725,883 and U.S. application Ser. No. 08/724,613 filed Sep. 30, 1996, now U.S. Pat. No. 5,725,884, which is a continuation of U.S. application Ser. No. 08/370,576, filed Jan. 9, 1995, now U.S. Pat. No. 5,585,115. The entire disclosures of U.S. application Ser. Nos. 08/660,553, 08/486,183, 08/724,613, and 08/370,576 are hereby incorporated by reference.

The present invention relates to a novel excipient for use in the manufacture of pharmaceuticals, and in particular, solid dosage forms such as tablets which include one or more active ingredients.

In order to prepare a solid dosage form containing one or more active ingredients (such as drugs), it is necessary that the material to be compressed into the dosage form possess certain physical characteristics which lend themselves to processing in such a manner. Among other things, the material to be compressed must be free-flowing, must be lubricated, and, importantly, must possess sufficient cohesiveness to insure that the solid dosage form remains intact after compression.

In the case of tablets, the tablet is formed by pressure being applied to the material to be tableted on a tablet press. A tablet press includes a lower punch which fits into a die from the bottom and a upper punch having a corresponding shape and dimension which enters the die cavity from the top after the tableting material fills the die cavity. The tablet is formed by pressure applied on the lower and upper punches. The ability of the material to flow freely into the die is important in order to insure that there is a uniform filling of the die and a continuous movement of the material from the source of the material, e.g. a feeder hopper. The lubricity of the material is crucial in the preparation of the solid dosage forms since the compressed material must be readily ejected from the punch faces.

Since most drugs have none or only some of these properties, methods of tablet formulation have been developed in order to impart these desirable characteristics to the material(s) which is to be compressed into a solid dosage form. Typically, the material to be compressed into a solid dosage form includes one or more excipients which impart the free-flowing, lubrication, and cohesive properties to the drug(s) which is being formulated into a dosage form.

Lubricants are typically added to avoid the material(s) being tableted from sticking to the punches. Commonly used lubricants include magnesium stearate and calcium stearate. Such lubricants are commonly included in the final tableted product in amounts of less than 1% by weight.

In addition to lubricants, solid dosage forms often contain diluents. Diluents are frequently added in order to increase the bulk weight of the material to be tableted in order to make the tablet a practical size for compression. This is often necessary where the dose of the drug is relatively small.

Another commonly used class of excipients in solid dosage forms are binders. Binders are agents which impart cohesive qualities to the powdered material(s). Commonly used binders include starch, and sugars such as sucrose, glucose, dextrose, and lactose.

Disintegrants are often included in order to ensure that the ultimately prepared compressed solid dosage form has an acceptable disintegration rate in an environment of use (such as the gastrointestinal tract). Typical disintegrants include starch derivatives and salts of carboxymethyl cellulose.

There are three general methods of preparation of the materials to be included in the solid dosage form prior to compression: (1) dry granulation; (2) direct compression; and (3) wet granulation.

Dry granulation procedures may be utilized where one of the constituents, either the drug or the diluent, has sufficient cohesive properties to be tableted. The method includes mixing the ingredients, slugging the ingredients, dry screening, lubricating and finally compressing the ingredients.

In direct compression, the powdered material(s) to be included in the solid dosage form is compressed directly without modifying the physical nature of the material itself.

The wet granulation procedure includes mixing the powders to be incorporated into the dosage form in, e.g., a twin shell blender or double-cone blender and thereafter adding solutions of a binding agent to the mixed powders to obtain a granulation. Thereafter, the damp mass is screened, e.g., in a 6- or 8-mesh screen and then dried, e.g., via tray drying, the use of a fluid-bed dryer, spray-dryer, radio-frequency dryer, microwave, vacuum, or infra-red dryer.

The use of direct compression is limited to those situations where the drug or active ingredient has a requisite crystalline structure and physical characteristics required for formation of a pharmaceutically acceptable tablet. On the other hand, it is well known in the art to include one or more excipients which make the direct compression method applicable to drugs or active ingredients which do not possess the requisite physical properties. For solid dosage forms wherein the drug itself is to be administered in a relatively high dose (e.g., the drug itself comprises a substantial portion of the total tablet weight), it is necessary that the drug(s) itself have sufficient physical characteristics (e.g., cohesiveness) for the ingredients to be directly compressed.

Typically, however, excipients are added to the formulation which impart good flow and compression characteristics to the material as a whole which is to be compressed. Such properties are typically imparted to these excipients via a pre-processing step such as wet granulation, slugging, spray drying, spheronization, or crystallization. Useful direct compression excipients include processed forms of cellulose, sugars, and dicalcium phosphate dihydrate, among others.

A processed cellulose, microcrystalline cellulose, has been utilized extensively in the pharmaceutical industry as a direct compression vehicle for solid dosage forms. Microcrystalline cellulose is commercially available under the tradename EMCOCEL® from Edward Mendell Co., Inc. and as Avicel® from FMC Corp. Compared to other directly compressible excipients, microcrystalline cellulose is generally considered to exhibit superior compressibility and disintegration properties.

Another limitation of direct compression as a method of tablet manufacture is the size of the tablet. If the amount of active ingredient is high, a pharmaceutical formulator may choose to wet granulate the active with other excipients to attain an acceptably sized tablet with the desired compact strength. Usually the amount of filler/binder or excipients needed in wet granulation is less than that required for direct compression since the process of wet granulation contributes to some extent toward the desired physical properties of a tablet. Thus, despite the advantages of direct compression (such as reduced processing times and costs), wet granulation is widely used in the industry in the preparation of solid dosage forms. Many of those skilled in the art prefer wet granulation as compared to direct compression because this method has a greater probability of overcoming any problems associated with the physical characteristics of the various ingredients in the formulation, thereby providing a material which has the requisite flow and cohesive characteristics necessary to obtain an acceptable solid dosage form.

The popularity of the wet granulation process as compared to the direct compression process is based on at least three advantages. First, wet granulation provides the material to be compressed with better wetting properties, particularly in the case of hydrophobic drug substances. The addition of a hydrophilic excipient makes the surface of a hydrophobic drug more hydrophilic, easing disintegration and dissolution. Second, the content uniformity of the solid dosage forms is generally improved. Via the wet granulation method, all of the granules thereby obtained should contain approximately the same amount of drug. Thus, segregation of the different ingredients of the material to be compressed (due to different physical characteristics such as density) is avoided. Segregation is a potential problem with the direct compression method. Finally, the particle size and shape of the particles comprising the granulate to be compressed are optimized via the wet granulation process. This is due to the fact that when a dry solid is wet granulated, the binder "glues" particles together, so that they agglomerate in the granules which are more or less spherical.

Due to the popularity of microcrystalline cellulose, pharmaceutical formulators have deemed it desirable to include this excipient in a formulation which is wet granulated prior to tableting. Unfortunately, currently-available microcrystalline cellulose does not hold to the typical principle that the amount of filler/binder needed in wet granulation is less than that in direct compression. It is known that the exposure of the microcrystalline cellulose to moisture in the wet granulation process severely reduces the compressibility of this excipient. The loss of compressibility of microcrystalline cellulose is particularly problematic where the formulation dictates that the final product will be relatively large in the environment of use. For example, if a pharmaceutical formulator desires to prepare a solid oral dosage form of a high dose drug, and the use of the wet granulation technique is deemed necessary, the loss of compressibility of the microcrystalline cellulose dictates that a larger amount of this material may be needed to obtain an acceptably compressed final product. The additional amount of microcrystalline cellulose needed adds cost to the preparation, but more importantly adds bulk, making the product more difficult to swallow.

The loss of compressibility of microcrystalline cellulose when exposed to wet granulation has long been considered a problem in the art for which there has been no satisfactory solution.

Attempts have been made to provide an excipient having high compressibility, a small bulk (high apparent density), and good flowability, while being capable of providing satisfactory disintegration of the solid dosage form, which is applicable to wet granulation as well as to dry granulation and direct compression methods for preparation of solid dosage forms.

For example, U.S. Pat. No. 4,159,345 (Takeo, et al.) describes an excipient which consists essentially of a microcrystalline cellulose having an average degree of polymerization of 60 to 375 and obtained through acid hydrolysis or alkaline oxidative degradation of a cellulosic substance selected from linters, pulps and regenerated fibers. The microcrystalline cellulose is said to be a white cellulosic powder having an apparent specific volume of 1.6–3.1 cc/g, a repose angle of 35° to 42°, a 200-mesh sieve residue of 2 to 80% by weight and a tapping apparent specific volume of at least 1.4 cc/g.

In U.S. Pat. No. 4,744,987 (Mehra, et al.), a particulate co-processed microcrystalline cellulose and calcium carbonate composition is described wherein the respective components are present in a weight ratio of 75:25 to 35:65. The co-processed composition is said to be prepared by forming a well-dispersed aqueous slurry of microcrystalline cellulose and calcium carbonate and then drying the slurry to yield a particulate product. The combination of these two ingredients is said to provide a lower cost excipient which has tableting characteristics similar to those of microcrystalline cellulose and which would satisfy a need for an economical excipient with good performance that is desired by the vitamin market.

European Patent Application EP 0609976A1 (assigned to Asahi Kasei Kabushiki Kaisha) describes an excipient comprising white powdery microcrystalline cellulose having an average degree of polymerization of from 100 to 375, preferably from 190 to 210, and an acetic acid holding capacity of 280% or more, preferably from 290 to 370%. The excipient is said to exhibit high compactability and a high rate of disintegration and is said to be obtained by heat-treating an aqueous dispersion of purified cellulose particles, which has a solids content of 40% or less by weight, at 100° C. or more, followed by drying, or by subjecting an aqueous dispersion of purified cellulose particles having a solids content of 23% or less by weight to thin film-forming treatment and drying the resultant thin film. The excipient is said to possess a high compressibility, and a good balance of compactability and rate of disintegration.

There still remains a need in the industry for a pharmaceutical excipient which possesses excellent compressibility whether utilized in a direct compression or wet granulation procedure.

OBJECTS AND SUMMARY OF THE INVENTION

It is an object of the present invention to provide an excipient which is useful in a variety of applications, and which may be utilized in direct compression or wet granulation methods.

It is a further object of the present invention to provide an excipient useful in direct compression methods which has improved compressibility relative to microcrystalline cellulose.

It is a further object of the present invention to provide an excipient useful in wet granulation methods which has improved compressibility relative to microcrystalline cellulose.

It is a further object of the present invention to provide a free-flowing excipient which has excellent compressibility properties when utilized in direct compression or wet granulation methods, and which furthermore possesses pharmaceutically acceptable disintegration properties.

It is a further object of the present invention to provide a free-flowing excipient which has excellent compressibility properties when utilized in direct compression or wet granulation methods, and which furthermore possesses pharmaceutically acceptable absorptive properties, e.g. enhanced bioavailability of the active agent from the gastrointestinal tract.

It is a further object of the present invention to provide an improved microcrystalline cellulose excipient in which the microcrystalline cellulose has not been chemically altered, and which has improved compressibility relative to "off-the-shelf" commercially available microcrystalline cellulose.

It is a further object of the present invention to provide a solid dosage form which includes one or more active agents and the improved microcrystalline cellulose excipient of the present invention.

It is a further object of the present invention to provide an oral solid dosage form for one or more drugs which is economical to manufacture, which maintains its integrity during storage, and which possesses excellent disintegration and dissolution properties when exposed, e.g., to gastrointestinal fluid.

In accordance with the above objects and others which will be obvious to those skilled in the art, the present invention is directed to an excipient comprising a particulate agglomerate of coprocessed microcrystalline cellulose and a compressibility augmenting agent. The novel agglomerated excipient preferably possesses compressibility at least equal to that of commercial grade microcrystalline cellulose, and preferably superior to that of commercial grade microcrystalline cellulose, when dry mixed or wet granulated with an active agent, other optional pharmaceutical additives and compressed into solid dosage forms.

The relative amount of compressibility augmenting agent coprocessed with the microcrystalline cellulose is dependent, in part, upon the type of compressibility augmenting agent selected. For purposes of the present invention, the amount is generally described as an effective amount, i.e. an amount which enhances or augments the compressibility of the microcrystalline cellulose. However, one skilled in the art will appreciate that in certain embodiments of the invention where improved or equal compressibility is not crucial to the preparation of the final solid dosage form, the agglomerated excipient may include an amount of augmenting agent which may not favorably affect compressibility but may instead impart a different beneficial result to the final product.

The microcrystalline cellulose and compressibility augmenting agent are in intimate association with each other, and the compressibility augmenting agent portion of the agglomerate is in the form of an aqueous solution or slurry prior to being coprocessed with microcrystalline cellulose.

The present invention is further directed to an agglomerated excipient which is derived from the aqueous slurry. The agglomerated excipient, which includes microcrystalline cellulose, at least one compressibility augmenting agent, and other optional ingredients, is dried in a manner which inhibits the formation of hydrogen bonds in the microcrystalline cellulose(intra-molecular and/or inter-molecular bonding). In other words, the compressibility augmenting agent is capable, during the drying of the aqueous slurry, of restricting the close approach of cellulose surfaces to each other by physically preventing these surfaces from approaching each other; or by changing the environment between these surfaces from an environment which tends to promote surface-to-surface interactions (such as hydrogen-bonding) to an environment which tends to inhibit such surface-to-surface interactions between surfaces of the microcrystalline cellulose. In certain embodiments, the compressibility of the microcrystalline cellulose is improved by utilizing one or more agents which are capable of both of these interactions with the microcrystalline cellulose.

Compressibility augmenting agents which create physical barriers between microcrystalline cellulose surfaces include silicon dioxide having a very fine particle size, e.g., from about 1 nm to about 100 $\mu$m. A most preferred silicon dioxide is colloidal silicon dioxide. Other materials of similar size may also be used instead of silicon dioxide to create the aforementioned physical barrier. In certain preferred embodiments, such other physically-acting compressibility augmenting agents will have at least some physical characteristics similar to that of silicon dioxide.

Compressibility augmenting agents which inhibit surface-to-surface interactions between surfaces of the microcrystalline cellulose include any material which has the ability, via a portion of the molecule, to bind or interact with the surface of the microcrystalline cellulose and at the same time, via another portion of the molecule, to inhibit the attraction of the cellulose surfaces, e.g., via a hydrophobic portion or "tail". Suitable compressibility augmenting agents will have an HLB value of at least 10, preferably at least about 15, and more preferably from about 15 to about 40 or greater. To date, compressibility augmenting agents which have shown the greatest effect have had relatively high HLB values, and therefore an HLB value from about 30 to about 40 or greater is most preferred. Agents which exhibit these properties include certain surfactants such as sodium lauryl sulfate and polysorbate 40, and highly polar compounds, including pharmaceutically acceptable dyes such as congo red.

The present invention is further directed to an aqueous slurry useful in the preparation of a compressible excipient useful in dry and wet granulation formulation methods, comprising a mixture of microcrystalline cellulose and compressibility augmenting agent. The solids content of the aqueous slurry is from about 0.5% to about 25%, by weight, preferably from about 15% to about 20% by weight, and most preferably from about 17% to about 19% by weight.

The present invention is further directed to a mixture of an active ingredient(s) and an excipient comprising a particulate agglomerate of coprocessed microcrystalline cellulose and a compressibility augmenting agent. The microcrystalline cellulose and compressibility augmenting agent are in intimate association with each other and the ratio of active ingredient to excipient is from about 1:99 to about 99:1, by weight.

The present invention is further directed to a granulate of an active agent and the novel excipient described herein, wherein the active agent and excipient have been subjected to a wet granulation procedure.

The present invention is also directed to a compressed solid dosage form comprising an active ingredient(s) and the novel excipient described herein, wherein the active agent and excipient have been directly compressed into the solid dosage form or have been subjected to a wet granulation procedure and thereafter compressed into the solid dosage form. The compressed solid dosage form provides a suitable release dissolution profile of the active ingredient(s) when exposed to aqueous solutions during in-vitro dissolution testing, and provides a release of drug in an environment of use which is considered bioavailable. In one embodiment of the invention, the dissolution profile of the solid dosage form is suitable for immediate release of the active agent. In further embodiments of the invention, the dissolution profile of the solid dosage form is modified to provide a controlled or sustained release dissolution profile.

The present invention is further directed to a method of maintaining and/or enhancing the compressibility of microcrystalline cellulose. The method includes forming an aqueous slurry containing a mixture of microcrystalline cellulose and a compressibility augmenting agent, and drying the slurry to obtain microcrystalline cellulose-based excipient particles in which the compressibility augmenting agent has been integrated with the microcrystalline cellulose particles. Within this aspect of the invention, the slurry contains from about 0.5% to about 25% by weight microcrystalline cellulose, with amounts of from about 15% to about 20% being preferred. The novel excipient described herein is free-flowing, possesses excellent disintegration and/or absorptive properties, and importantly, in certain embodiments possesses improved compressibility relative to normal "off-the-shelf" commercially available microcrystalline cellulose when directly compressed. The advantages of the novel excipient described herein are especially realized in pharmaceutical formulations prepared using wet granulation techniques. When utilized in wet granulation techniques, the novel excipient surprisingly provides a compressibility which is substantially improved in preferred embodiments in comparison to the compressibility of normal "off-the-shelf" commercially available microcrystalline cellulose used in wet granulation and is even comparable to "off-the-shelf" microcrystalline cellulose used in direct compression techniques. In other embodiments, the novel excipient surprisingly provides a compressibility which is substantially superior to the compressibility of normal "off-the-shelf" commercially available microcrystalline cellulose used in direct compression techniques.

Accordingly, the novel agglomerated of the invention provides enhanced material flow properties and direct compression compactibility compared to regular microcrystalline cellulose. The enhanced compactibility has been shown to allow for the production of satisfactory tablets, even with poorly compactible drugs, reduction in tablet size for various high dose drug formulations, and, in general, enhancement of the drug content uniformity of tableted dosage forms, especially in high speed tableting.

The term "environmental fluid" is meant for purposes of the invention to encompass, e.g., an aqueous solution, or gastrointestinal fluid.

By "bioavailable" it is meant for purposes of the invention that the therapeutically active medicament is absorbed from the solid dosage form which includes the novel agglomerated excipient of the invention, and becomes available in the body at the intended site of drug action.

By "surfactant" it is meant for purposes of the present invention that the material is a surface active agent which displays wetting, detergent or soap-like qualities as those agents are understood by those of ordinary skill in the art.

The benefits of the novel agglomerated microcrystalline cellulose excipients of the invention include higher direct compression compactibility (which in turn provides harder, less friable tablets, reduces binder usage/cost, reduces tablet size, and accommodates poorly compactible active ingredients), and enhanced material flow (which in turn provides better content uniformity, allows higher speed tableting, and accommodates poorly flowing drugs); and preservation of compactibility in a wet granulation (which in turn reduces formulation development time and cost, reduces binder usage/cost, avoids extra-granular processing/cost, and reduces tablet size).

BRIEF DESCRIPTION OF THE DRAWINGS

The following drawings are illustrative of embodiments of the invention and are not meant to limit the scope of the invention as encompassed by the claims.

DETAILED DESCRIPTION OF THE INVENTION

Figure 1:
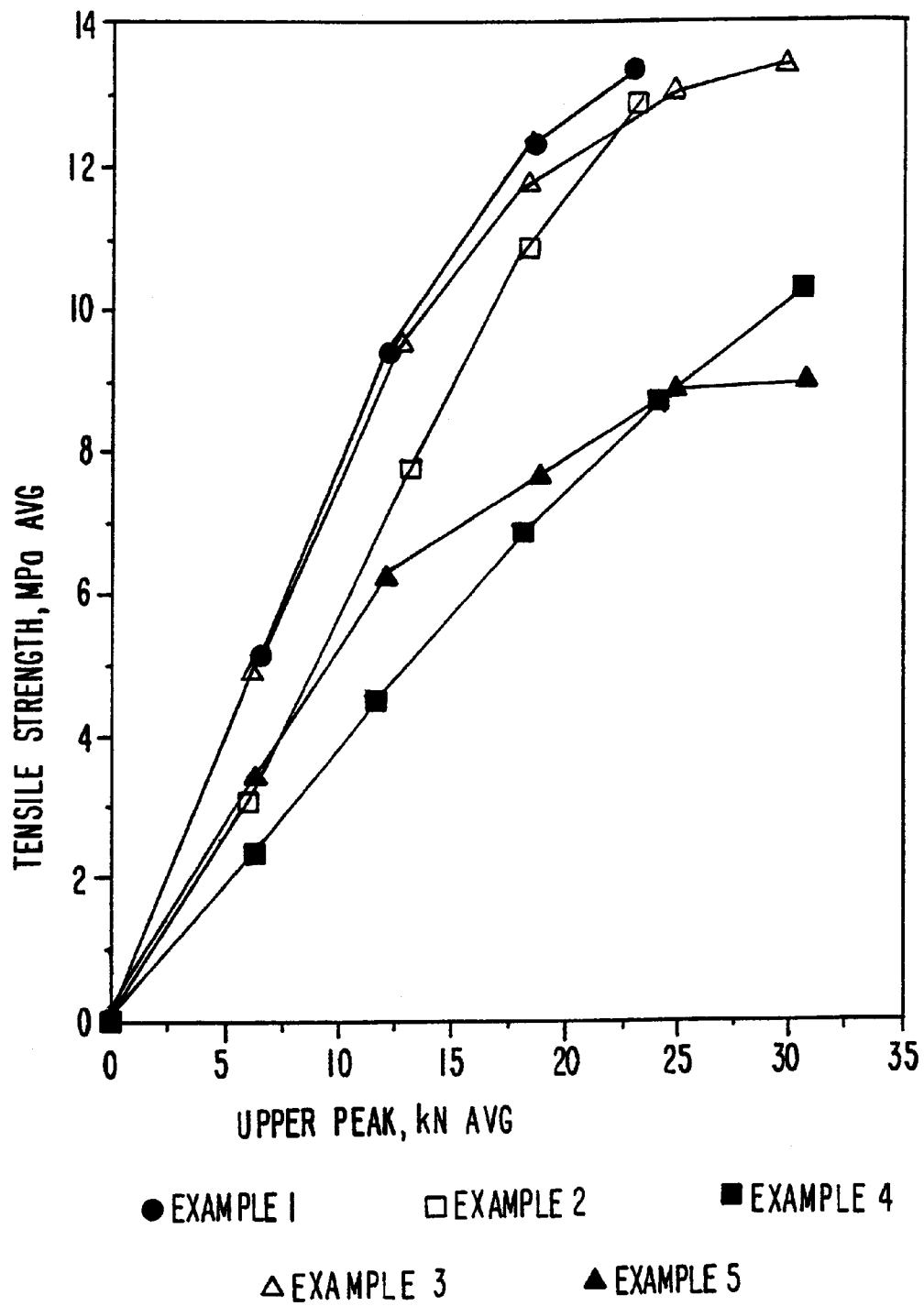
FIG. 1 graphically shows a comparison of the tensile strength of tablets prepared in accordance with the invention and (compressibility augmenting agent=silicon dioxide) prior art tablets.

Excipients of the present invention comprise Microcrystalline Cellulose (MCC) and augmenting agents. Microcrystalline cellulose is a well-known tablet diluent, binder and disintegrant. Its chief advantage over other excipients is that it can be directly compressed into self-binding tablets which disintegrate rapidly when placed into water. This widely-used ingredient is prepared by partially depolymerizing cellulose obtained as a pulp from fibrous plant material with dilute mineral acid solutions. Following hydrolysis, the hydrocellulose thereby obtained is purified via filtration and an aqueous slurry is spray dried to form dry, white odorless, tasteless crystalline powder of porous particles of various sizes. Another method of preparing microcrystalline cellulose is disclosed in U.S. Pat. No. 3,141,875. This reference discloses subjecting cellulose to the hydrolytic action of hydrochloric acid at boiling temperatures so that amorphous cellulosic material can be removed and aggregates of crystalline cellulose are formed. The aggregates are collected by filtration, washed with water and aqueous ammonia and disintegrated into small fragments, often called cellulose crystallites by vigorous mechanical means such as a blender. Microcrystalline cellulose is commercially available in several grades which range in average particle size from 20 to 200 microns.

Microcrystalline cellulose is water-insoluble, but the material has the ability to draw fluid into a tablet by capillary action. The tablets then swell on contact and the microcrystalline cellulose thus acts as a disintegrating agent. The material has sufficient self-lubricating qualities so as to allow a lower level of lubricant as compared to other excipients.

Typically, microcrystalline cellulose has an apparent density of about 0.28 $g/cm^3$ and a tap density of about 0.43 $g/cm^3$. *Handbook of Pharmaceutical Excipients,* pages 53–55.

When utilized in pharmaceutical applications, microcrystalline cellulose is typically used as a tablet binder/diluent in wet granulation and direct compression formulations in amounts of 3–30% of the formulation, or more. However, it is known to use more or less microcrystalline cellulose in pharmaceutical products, depending upon the requirements of the formulation.

The novel excipients of the present invention also include one or more compressibility augmenting agents. The compressibility augmenting agent(s) is present in amounts ranging from about 0.1% to about 50% by weight of microcrystalline cellulose.

Direct compression tablet manufacturing is preferred for many products in the pharmaceutical industry. It is a simple process involving less extensive equipment, operating time and cost. Microcrystalline cellulose is a good excipient for direct compression processing.

Microcrystalline cellulose has inherently high compactibility due to its plastic deformation and limited elastic recovery. Microcrystalline cellulose usually provides for good drug dispersion, even ordered mixing with some drugs and particular grades of microcrystalline cellulose. However, the material flow properties are relatively poor for most grades of microcrystalline cellulose. Intermittent and non-uniform flow can occur as the formulation moves from the hopper to the die on a tablet press. This non-uniform flow can lead to drug content variations in the finished tableted dosage form.

The popularity of the wet granulation process as compared to the direct compression process is based on at least three potential advantages. First, wet granulation may provide the material to be compacted with a more hydrophilic nature, in order to improve the wetting, disintegration and dissolution characteristics of some hydrophobic drugs or ingredients. Second, the content uniformity and drug segregation-resistance can be enhanced using a granulation step to lock drug and excipient components together during blending. Finally, the micrometric characteristics of the component powders can be optimized prior to compaction, which is often aided by incorporation of a polymeric binder. It is normally considered that this last property imbued by wet granulation will yield a significantly more compactible product and consequently stronger, more robust tablets. However, it has been found that the most compactable tableting excipient, microcrystalline cellulose, can lose between 30 and 50% of its tablet strength enhancing characteristics, following wet granulation. Microcrystalline cellulose tablet weakening caused by wet granulation is observed in all cases where water is added, although the magnitude of loss of compactibility is directed related to the concentration of water used, as well as granulation and drying energetics. This loss of compactibility can result in a very significant loss of functionality, generally leading to a requirement for a larger binder concentration in the formulation and consequently less efficient and more costly tablet production as well as larger tablets.

We have found that the reduction in compactibility of microcrystalline cellulose which has been wet granulated is generally accompanied by a decrease in particle porosity, specific surface area available to adsorb nitrogen and also an increase in granule bulk density and friability. However, granule particle size distribution was found to have a relatively minor effect on granule compactibility. Wet granulation has been found to have only a minor effect on the solubility parameters of microcrystalline cellulose. Further, wet granulation does not alter the X-ray diffraction pattern and the Raman and 13C-NMR spectra of microcrystalline cellulose. However, as a result of granulation, the infrared spectra of microcrystalline cellulose obtained using the techniques of attenuated total reflectance (ATRIR) and optical IR spectroscopy were altered slightly. This is hypothesized to indicate that only the near-surface molecular layers may be significantly involved in interactions with water. Granule properties, including compactibility, have also been found to be influenced by the amount of granulating fluid employed, the duration and rate of wet mass agitation, wet mass storage time before drying, and granule drying technique. Further, granule dewatering by solvent exchange was found to have a beneficial effect on granule compactibility.

It is hypothesized that the granulation-reduced microcrystalline cellulose compactibility is caused at least in significant part by increasing intraparticle and/or interparticle hydrogen bonding. For purposes of the present invention, this phenomenon is termed "quasi-hornification" since, unlike hornification of cellulose fibers described in the literature elsewhere, quasi-hornification of microcrystalline cellulose has not ben observed by us to reduce the ability of microcrystalline cellulose to absorb water vapor. Furthermore, quasi-hornified microcrystalline cellulose was found to be fully reversible, unlike the hornification which occurs when cellulose is wetted. Microcalorimetry indicates that during adsorption of water vapor by granulated microcrystalline cellulose, the extent of intraparticle bond disruption is greater than occurring during water vapor adsorption by ungranulated microcrystalline cellulose. This provides evidence to support the theory that granulation results in increased intraparticle hydrogen bonding, some of which is reversible on adsorption of water vapor.

The present invention is directed in part to a novel agglomerated microcrystalline cellulose excipient which comprises a combination of microcrystalline cellulose as described above together in intimate association with a compressibility augmenting agent. The novel agglomerated microcrystalline cellulose excipient is prepared in a manner which significantly reduces the hydrogen bonding between inter- and/or intra-molecular cellulose-to-cellulose bonding which occurs when regular, commercial grade microcrystalline cellulose is exposed to moisture (water). This can be accomplished, e.g., by preparing an aqueous slurry of microcrystalline cellulose, compressibility augmenting agent(s), and other optional ingredients, and drying the mixture in a manner which inhibits quasi-hornification.

The novel agglomerated microcrystalline cellulose excipient utilizes a compressibility augmenting agent which (i) physically restricts the proximity of the interface between adjacent cellulose surfaces;

(ii) inhibits interactions between adjacent cellulose surfaces, for example, via the creation of a hydrophobic boundary at cellulose surfaces; or (iii) accomplishes both (i) and (ii) above.

In one preferred embodiment of the invention, the compressibility augmenting agent which provides a physical barrier between adjacent cellulose surfaces is a silicon dioxide. Silicon dioxide is obtained by insolubilizing dissolved silica in sodium silicate solution. When obtained by the addition of sodium silicate to a mineral acid, the product is termed silica gel. When obtained by the destabilization of a solution of sodium silicate in such a manner as to yield very fine particles, the product is termed precipitated silica. Silicon dioxide is insoluble in water. Prior to the present invention, silicon dioxide, and in particular colloidal silicon dioxide, was used mainly as a glidant and anti-adherent in tableting processes and encapsulation, promoting the flowability of the granulation. The amount of silicon dioxide included in such tablets for those applications is very limited, 0.1–0.5% by weight. Handbook of Pharmaceutical Excipients, ©1986 American Pharmaceutical Association, page 255. This is due in part to the fact that increasing the amount of silicon dioxide in the mixture to be tableted causes the mixture to flow too well, causing a phenomena known to those skilled in the tableting art as "flooding". If the mixture flows too well, a varying tablet weight with uneven content uniformity can result.

Those skilled in the art will appreciate that the name and/or method of preparation of the silicon dioxide utilized in the present invention is not determinative of the usefulness of the product. Rather, as previously mentioned, it has been surprisingly discovered that it is the physical characteristics of the silicon dioxide that are critical. In particular, it has been discovered that silicon dioxide having a relatively large particle size (and correspondingly small surface area), such as silica gel, is not useful in the preparation of the improved microcrystalline cellulose products of the invention. The appended claims are deemed to encompass all forms of silicon dioxide having an average primary particle size from about 1 nm to about 100 $\mu$m, and/or a surface area from about 10 $m^2$/g to about 500 $m^2$/g.

The silicon dioxide utilized in the invention is of the very fine particle size variety. In the more preferred embodiments of the invention, the silicon dioxide utilized is a colloidal silicon dioxide. Colloidal silicon dioxide is a submicron fumed silica prepared by the vapor-phase hydrolysis (e.g., at 1110° C.) of a silicon compound, such as silicon tetrachloride. The product itself is a submicron, fluffy, light, loose, bluish-white, odorless and tasteless amorphous powder which is commercially available from a number of sources, including Cabot Corporation (under the tradename Cab-O-Sil); Degussa, Inc. (under the tradename Aerosil); E. I. DuPont & Co.; and W. R. Grace & Co. Colloidal silicon dioxide is also known as colloidal silica, fumed silica, light anhydrous silicic acid, silicic anhydride, and silicon dioxide fumed, among others. A variety of commercial grades of colloidal silicon dioxide are produced by varying the manufacturing process. These modifications do not affect the silica content, specific gravity, refractive index, color or amorphous form. However, these modifications are known to change the particle size, surface areas, and bulk densities of the colloidal silicon dioxide products.

The surface area of the preferred class of silicon dioxides utilized in the invention ranges from about 50 $m^2$/gm to about 500 $m^2$/gm. The average primary particle diameter of the preferred class of silicon dioxides utilized in the invention ranges from about 5 nm to about 50 nm. However, in commercial colloidal silicon dioxide products, these particles are agglomerated or aggregated to varying extents. The bulk density of the preferred class of silicon dioxides utilized in the invention ranges from about 20 g/l to about 100 g/l.

Commercially available colloidal silicon dioxide products have, for example, a BET surface area ranging from about 50±15 $m^2$/gm (Aerosil OX50) to about 400±20 (Cab-O-Sil S-17) or 390±40 $m^2$l/gm (Cab-O-Sil EH-5). Commercially available particle sizes range from a nominal particle diameter of 7 nm (e.g., Cab-O-Sil S-17 or Cab-O-Sil EH-5) to an average primary particle size of 40 nm (Aerosil OX50). The density of these products range from 72.0±8 g/l (Cab-O-Sil S-17) to 36.8 g/l (e.g., Cab-O-Sil M-5). The pH of the these products at 4% aqueous dispersion ranges from pH 3.5–4.5. These commercially available products are described for exemplification purposes of acceptable properties of the preferred class of silicon dioxides only, and this description is not meant to limit the scope of the invention in any manner whatsoever.

When the novel excipient of the invention utilizes a colloidal silicon dioxide, it has been found that the resultant excipient product surprisingly provides a compressibility which is substantially improved in preferred embodiments even in comparison to the compressibility of normal "off-the-shelf" commercially available microcrystalline cellulose used in direct compression techniques.

In other embodiments of the present invention, it has been discovered that the compressibility of microcrystalline cellulose which is wet granulated is significantly improved by a wider range of silicon dioxide products. Thus, in embodiments of the present invention where an improvement in overall compressibility of the microcrystalline cellulose (whether utilized in wet granulation or dry granulation) is not important, and the microcrystalline cellulose product is to be subjected to wet granulation, it has been discovered that the surface area of the silicon dioxide can be as low as about 50 $m^2$/gm and the average primary particle diameter can be as large as about 100 $\mu$m. Such silicon dioxide products are also deemed to be encompassed within the scope of the invention.

The coprocessed product consists of microcrystalline cellulose and silicon dioxide in intimate association with each other. Magnifications of the resultant particles indicate that the silicon dioxide is integrated with, or partially coats, the surfaces of the microcrystalline cellulose particles. When the amount of silicon dioxide included in the excipient is greater than about 20% by weight relative to the microcrystalline cellulose, the silicon dioxide appears to substantially coat the surfaces of the microcrystalline cellulose particles. The exact relationship of the two ingredients of the excipients after coprocessing is not presently understood; however, for purposes of description the coprocessed particles are described herein as including an agglomerate of microcrystalline cellulose and silicon dioxide in intimate association with each other. The coprocessed particles are not necessarily uniform or homogeneous. Rather, under magnification, e.g., scanning electron microscope at 500×, the silicon dioxide at the preferred percent inclusion appears to be an "edge-coating".

Depending upon the amount and type of drying, the concentration of the microcrystalline cellulose and silicon dioxide in the suspension, the novel compressible particles will have different particle sizes, densities, pH, moisture content, etc.

The particulate coprocessed product of this aspect of the present invention possesses desirable performance attributes that are not present when the combination of microcrystalline cellulose and silicon dioxide are combined as a dry mixture. It is believed that the beneficial result obtained by the combination of these two materials is due to the fact that the two materials are intimately associated with each other.

One skilled in the art will appreciate that other classes of compounds having size, surface area, and other similar physical characteristics to silicon dioxide may be useful in physically forming a barrier which may reduce the surface-to-surface interactions (including hydrogen-bonding) between cellulose surfaces. Such materials include (but are not limited to) non-silicon metal oxides, preferably colloidal. Such obvious modifications of the present invention are deemed to be within the contemplated scope of the appended claims.

In other preferred embodiments of the invention, the compressibility augmenting agent is a material which inhibits interactions between adjacent cellulose surfaces, for example, via the creation of a hydrophobic boundary or barrier at cellulose surfaces. As previously mentioned, compressibility augmenting agents which inhibit surface-to-surface interactions between surfaces of the microcrystalline cellulose include any material which has the ability, via a portion of the molecule, to bind or interact with the surface of the microcrystalline cellulose and at the same time, via another portion of the molecule, to inhibit the attraction of the cellulose surfaces, e.g., via a hydrophobic portion or "tail". Suitable compressibility augmenting agents will have an HLB value of at least 10, preferably at least about 15, and more preferably from about 15 to about 40 or greater. Compressibility augmenting agents having an HLB value from about 30 to about 40 or greater is most preferred.

Surfactants which may be used in the present invention as a compressibility augmenting agent generally include all pharmaceutically-acceptable surfactants, with the proviso that the surfactant have an HLB value of at least 10, and preferably at least about 15.

In certain preferred embodiments, the HLB value of the surfactant is from about 15 to 50, and in further embodiments is most preferably from about 15.6 to about 40. Suitable pharmaceutically-acceptable anionic surfactants include, for example, those containing carboxylate, sulfonate, and sulfate ions. Those containing carboxylate ions are sometimes referred to as soaps and are generally prepared by saponification of natural fatty acid glycerides in alkaline solutions. The most common cations associated with these surfactants are sodium, potassium, ammonium and triethanolamine. The chain length of the fatty acids range from 12 to 18. Although a large number of alkyl sulfates are available as surfactants, one particularly preferred surfactant is sodium lauryl sulfate, which has an HLB value of about 40.

In the pharmaceutical arts, sodium lauryl sulfate has been used as an emulsifying agent in amounts of up to about 0.1% by weight of the formulation. However, surfactants such as sodium lauryl sulfate have been included in coprocessed microcrystalline cellulose compositions. Moreover, surfactants have been used in the amounts described herein to improve the compressibility of microcrystalline cellulose especially in wet granulations. Sodium lauryl sulfate is a water-soluble salt, produced as a white or cream powder, crystals, or flakes and is used as a wetting agent and detergent. Also known as dodecyl sodium sulfate, sodium lauryl sulfate is actually a mixture of sodium alkyl sulfates consisting chiefly of sodium lauryl sulfate. Sodium lauryl sulfate is also known as sulfuric acid monododecyl ester sodium salt. Furthermore, sodium lauryl sulfate is readily available from commercial sources such as Sigma or Aldrich in both solid form and as a solution. The solubility of sodium lauryl sulfate is about 1 gm per 10 ml/water. The fatty acids of coconut oil, consisting chiefly of lauric acid, are catalytically hydrogenated to form the corresponding alcohols. The alcohols are then esterified with sulfuric acid (sulfated) and the resulting mixture of alkyl bisulfates (alkyl sulfuric acids) is converted into sodium salts by reacting with alkali under controlled conditions of pH.

Alternative anionic surfactants include docusate salts such as the sodium salt thereof. Other suitable anionic surfactants include, without limitation, alkyl carboxylates, acyl lactylates, alkyl ether carboxylates, N-acyl sarcosinates, polyvalent alkyl carbonates, N-acyl glutamates, fatty acid, polypeptide condensates and sulfuric acid esters.

In other aspects of the invention amphoteric (amphipathic/amphiphilic surfactants), non-ionic surfactants and/or cationic surfactants are included in the coprocessed compositions of the invention. Suitable pharmaceutically-acceptable non-ionic surfactants such as, for example, polyoxyethylene compounds, lecithin, ethoxylated alcohols, ethoxylated esters, ethoxylated amides, polyoxypropylene compounds, propoxylated alcohols, ethoxylated/propoxylated block polymers, propoxylated esters, alkanolamides, amine oxides, fatty acid esters of polyhydric alcohols, ethylene glycol esters, diethylene glycol esters, propylene glycol esters, glycerol esters, polyglycerol fatty acid esters, SPAN's (e.g., sorbitan esters), TWEEN's (i.e., sucrose esters), glucose (dextrose) esters and simethicone. The HLB for one acceptable non-ionic surfactant, polysorbate 40, is about 15.6.

Other suitable pharmaceutically-acceptable surfactants include acacia, benzalkonium chloride, cholesterol, emulsifying wax, glycerol monostearate, lanolin alcohols, lecithin, poloxamer, polyoxyethylene, and castor oil derivatives.

Those skilled in the art will further appreciate that the name and/or method of preparation of the surfactant utilized in the present invention is not determinative of the usefulness of the product. Rather, as previously mentioned, it has been surprisingly discovered that it is the physical characteristics of surfactants, especially those of the anionic class such as sodium lauryl sulfate, which are critical. In particular, it has been discovered that when an anionic surfactant such as sodium lauryl sulfate is coprocessed with microcrystalline cellulose in the amounts described herein, improved microcrystalline cellulose products of the invention result.

When the novel excipient of the invention utilizes an anionic surfactant, it has been found that the resultant excipient product surprisingly provides a compressibility which is substantially improved in preferred embodiments even in comparison to the compressibility of normal "off-the-shelf" commercially available microcrystalline cellulose used in direct compression techniques. In other embodiments of the present invention, it has been discovered that the compressibility of microcrystalline cellulose which is wet granulated is significantly improved by coprocessing the microcrystalline cellulose with an anionic surfactant such as sodium lauryl sulfate.

Since microcrystalline cellulose is substantially water insoluble, the particle size of this ingredient in the well-dispersed aqueous slurry is directly related to its particle size as it was introduced into the aqueous solution. Most surfactants, on the other hand, tend to be water soluble. Sodium lauryl sulfate, for example, is relatively soluble in water (1 g/10 ml) and, therefore, dissolves in the aqueous slurry. It should be understood, however, that the coprocessed products of the present invention are not solely limited to those which contain a dissolved surfactant. The contemplated compositions can also be prepared from slurries which contain a dispersion of the surfactant as well as the microcrystalline cellulose.

Highly polar molecules having the requisite HLB value range set forth above may also be utilized as the compressibility augmenting agent. Such highly polar molecules include certain dyes, particular those which may be capable of binding to the cellulose surface while thereafter creating a relatively hydrophobic environment due to the presence of a hydrophobic portion of the molecule (e.g., a hydrophobic tail) which "points away" from the cellulose surface and discourages hydrophilic surface-to-surface cellulose interactions, such as hydrogen-bonding. Preferably, the dye is one which is pharmaceutically acceptable for inclusion in solid dosage forms.

Examples of suitable dyes include Congo Red (chemical name: 3,3'-[[1,1'Biphenyl]-4,4'-diylbis-(azo)]bis[4-amino-1-naphthalenesulfonic acid] disodium salt; FD&C Red No. 40 (also known as "Allura Red") (chemical name: Disodium salt of 6-hydroxy-5[(2-methyl-4-sulfophenyl)azo]-2-naphthalenesulfonic acid); FD&C Yellow No. 5 (common name: tartrazine) (chemical name: 5-oxo-1-(p-sulfophenyl)-4-[(p-sulfophenyl)azo]-2-pyrazoline-3-carboxylic acid, trisodium salt); FD&C Yellow No. 6 (common name: Sunset Yellow FCF) (chemical name: Disodium salt of 1-p-sulphophenylazo-2-naphthol-6-sulfonic acid); Ponceau 4R (chemical name: Trisodium-2-hydroxy-1-(4-sulfonato-1-naphthylazo)naphthalene-6,8-disulfonate); Brown HT (chemical name: Disodium 4,4'-(2,4-dihydroxy-5-hydroxymethyl-3,3-phenylene bisazo)di(napthalene-1-sulfonate)); Brilliant Black BN (Chemical name: Tetrasodium 4-acetamido-5-hyroxy-6-[7-sulfonato-4-(4-sulfonatophenylazo)-1-naphthylazo]naphthalene-1,7-disulfonate); Carmoisine (chemical name: Disodium 4-hydroxy-3-(4-sulfanato-1-naphythylazo) Naphthalene-1-sulfonate); Amaranth (chemical name: Trisodium 2-hydroxy-1-(4-sulfonato-1-naphthylazo)naphthalene-3,6-disulfonate); and mixtures thereof.

Other highly polar molecules having the requisite HLB value range set forth above which may be utilized as the compressibility augmenting agent include the active agents themselves. For example, it is well-known to those skilled in the art that certain classes of pharmaceuticals, such as anti-pyschotic drugs, are highly polar in nature and may be utilized as a compressibility augmenting agent in accordance with this invention.

One skilled in the art will appreciate that other classes of highly polar compounds may be useful in reducing the surface-to-surface interactions (including hydrogen-bonding) between cellulose surfaces. Such obvious modifications of the present invention are deemed to be within the contemplated scope of the appended claims.

It is preferred in the present invention that the microcrystalline cellulose and compressibility augmenting agent are coprocessed, resulting in an intimate association of these ingredients, rather than being combined, e.g., as a dry mixture. In preferred embodiments of the present invention, an aqueous slurry of the microcrystalline cellulose, the compressibility augmenting agent(s) and other optional ingredients is prepared in order to obtain (after a drying step) agglomerated particles wherein these components are intimately associated. The aqueous slurry of the microcrystalline cellulose and compressibility augmenting agent are introduced into the spray dryer as a single aqueous medium. However, it is possible to separately introduce each ingredient into separate aqueous medium which are then combined. Other procedures for combining these materials with or without other optional ingredients known to those skilled in the art are deemed to be equivalent to the spray-drying technique described above, and are further deemed to be encompassed by the appended claims.

In preferred embodiments of the present invention, the coprocessing of the microcrystalline cellulose and compressibility augmenting agent is accomplished by forming a well-dispersed aqueous slurry of microcrystalline cellulose in which the compressibility augmenting agent has been dissolved, and thereafter drying the slurry and forming a plurality of microcrystalline cellulose-based excipient particles. Typically, microcrystalline cellulose is first added to an aqueous solution so that a slurry or suspension containing from about 0.5% to about 25% microcrystalline cellulose in the form of solids is obtained. Preferably, the slurry or suspension contains from about 15% to 20% microcrystalline cellulose and most preferably from about 17% to about 19% microcrystalline cellulose. At this stage, it is optionally desirable to adjust the pH of the slurry to about neutral with ammonium hydroxide, sodium hydroxide, and mixtures thereof or the like. The suspension is kept under constant agitation for a sufficient time to assure a uniform distribution of the solids prior to being combined with the compressibility augmenting agent.

For example, silicon dioxide is added to the suspension or slurry in amounts ranging from 0.1% to about 20% by weight, based on the amount of microcrystalline cellulose, amounts from about 0.5% to about 10% are preferred while amounts of from about 1.25% to about 5% by weight are especially preferred. There is no appreciable dissolution of either ingredient (microcrystalline cellulose or silicon dioxide), since both are relatively water insoluble. The microcrystalline cellulose and silicon dioxide are well-dispersed in the slurry or suspension prior to drying and forming the novel particles.

On the other hand, the surfactant is added to the suspension or slurry in amounts ranging from about 0.1% to about 20% by weight, preferably from about 0.1 to about 5% by weight, based on the amount of microcrystalline cellulose, and in certain embodiments preferably from about 0.15% to about 0.4%, by weight. When the surfactant is sodium lauryl sulfate, the amount is most preferably from about 0.2 to about 0.3%, by weight. The surfactant can be added to the suspension as either a solid or in solution form. The microcrystalline cellulose is thus well-dispersed in the slurry or suspension and the surfactant is dissolved therein prior drying and forming the novel particles. It will be understood that other useful surfactants can be used in like amounts or even greater amounts, i.e. up to 20% by weight or even more. The usable concentration range for the selected surfactant depends in part upon not only its molecular weight but also its degree of foaming, particularly when present in agitated slurries which will be spray dried to form the desired particulate. Thus, in those aspects of the invention where surfactants other than sodium lauryl sulfate are coprocessed with the microcrystalline cellulose, it is to be understood that the surfactant will be present in an amount which enhances the compressibility of the Microcrystalline cellulose and yet does not have a degree of foaming which would substantially inhibit spray drying.

Other compressibility augmenting agents (including highly polar dyes, highly polar drugs, and other useful materials having a HLB from about 15 to about 50) may be included in the aqueous slurry in amounts ranging from about 0.1% to about 20%, by weight, and more preferably from about 0.5 to about 10%, by weight.

After a uniform mixture of the ingredients is obtained in the suspension, the suspension is dried to provide a plurality of microcrystalline cellulose-based excipient particles having enhanced compressibility (e.g., dried in a manner which inhibits quasi-hornification).

In the (preferred) spray-drying process, the aqueous dispersion of microcrystalline cellulose and surfactant is brought together with a sufficient volume of hot air to produce evaporation and drying of the liquid droplets. The highly dispersed slurry of microcrystalline cellulose and surfactant is pumpable and capable of being atomized. It is sprayed into a current of warm filtered air, which supplies the heat for evaporation and conveys a dried product to a collecting device. The air is then exhausted with the removed moisture. The resultant spray-dried powder particles are approximately spherical in shape and are relatively uniform in size, thereby possessing excellent flowability. The coprocessed product consists of microcrystalline cellulose and surfactant in intimate association with each other. The exact relationship of the two ingredients of the excipients after coprocessing is not presently understood; however, for purposes of description the coprocessed particles are described herein as including an agglomerate of microcrystalline cellulose and surfactant in intimate association with each other. By "intimate associate", it is meant that the surfactant has in some manner been integrated with the microcrystalline cellulose particles, e.g., via a partial coating of the microcrystalline particles, as opposed to a chemical interaction of the two ingredients. The term "intimate association" is therefore deemed for purposes of the present description as being synonymous with "integrated" or "united". The coprocessed particles are not necessarily uniform or homogeneous.

It is preferred that the suspension be dried using spray-drying techniques, as they are known in the art. Other drying techniques, however, such as flash drying, ring drying, micron drying, tray drying, vacuum drying, radio-frequency drying, and possibly microwave drying, may also be used, although spray drying is preferred.

Depending upon the amount and type of drying, the concentration of the microcrystalline cellulose and compressibility augmenting agent in the suspension, the novel compressible particles will have different particle sizes, densities, pH, moisture content, etc.

The particulate coprocessed product of the present invention possesses desirable performance attributes that are not present when the combination of microcrystalline cellulose and compressibility augmenting agent are combined as a dry mixture. It is believed that the beneficial result obtained by the combination of these two materials is due to the fact that the two materials are intimately associated with each other. It has also been found that intimate association of Microcrystalline cellulose and other detergent-like materials such as simethicone, even when they are dissolved/dispersed in the aqueous solutions which form the Microcrystalline cellulose slurry, fail to provide Microcrystalline cellulose with enhanced compressibility.

The average particle size of the agglomerated microcrystalline cellulose excipient of the present invention ranges from about 10 microns to about 1000 microns. Particle sizes of about 10–500 microns are preferred, particle sizes of about 30–250 microns are more preferred and particle sizes of about 40–200 microns are most preferred. It will be appreciated by those of ordinary skill in the art that the drying of the aqueous suspension results in a random size distribution of the novel excipient particles being produced. For example, if spray drying techniques are used, droplet size, temperatures, agitation, dispersion, air flow, atomizer wheel speed, etc. will effect final particle size. Furthermore, it is within the scope of the invention to sort or mechanically alter the dried particles according to ranges of particle sizes depending upon end uses. The particle size of the integrated excipient is not narrowly critical, the important parameter being that the average size of the particle must permit the formation of a directly compressible excipient which forms pharmaceutically acceptable tablets.

The novel agglomerated microcrystalline cellulose excipient has a bulk (loose) density ranging from about 0.2 g/ml to about 0.6 g/ml, and most preferably from about 0.22 g/ml to about 0.55 g/ml. The novel excipient has a tapped density ranging from about 0.20 g/ml to about 0.70 g/ml, and most preferably from about 0.35 g/ml to about 0.60 g/ml. The pH of the particles is most preferably about neutral, although granulates having a pH of from about 3.0 to about 8.5 are possible. The moisture content of the excipient particles will broadly range from about 0.5% to about 15%, preferably from about 2.5% to about 6%, and most preferably from about 3.0% to about 5% by weight.

The angle of repose is a measurement used to determine the flow characteristics of a powder. The angle of repose is subject to experiment and experimenter, but in a comparative test, the novel excipient is superior.

The novel agglomerated microcrystalline cellulose excipient of the invention is free-flowing and directly compressible. Accordingly, the excipient may be mixed in the desired proportion with an active agent and optional lubricant (dry granulation), and then directly compressed into solid dosage forms. In preferred embodiments of the present invention wherein the surfactant is sodium lauryl sulfate, the novel excipient represents an augmented microcrystalline cellulose having improved compressibility as compared to standard commercially available grades of microcrystalline cellulose.

Alternatively, all or part of the excipient may be subjected to a wet granulation with the active ingredient. A representative wet granulation includes loading the novel excipient particles into a suitable granulator, such as those available from Baker-Perkins, and granulating the particles together with the active ingredient, preferably using an aqueous granulating liquid. The granulating liquid is added to the mixture with stirring until the powdery mass has the consistency of damp snow and then wet screened through a desired mesh screen, for example, having a mesh from about 12 to about 16. The screened granulate is then dried, using standard drying apparatus such as a convection oven before undergoing a final screening. Additional dry screening of this material is possible, such as by using screens of from about 40 to about 200 mesh. Those materials flowing through 40 and 60 mesh screens may be further ground prior to ultimate tablet formulation. The thus obtained granulate containing the novel excipient is now capable of undergoing tableting or otherwise placed into a unit dosage form.

In certain preferred embodiments, a portion of the total amount of the novel excipient is wet granulated with the active ingredient, and thereafter the additional portion of the novel excipient is added to the granulate. In yet other embodiments, the additional portion of the novel excipient to be added to the excipient/active ingredient granulate may be substituted with conventional microcrystalline cellulose, or other excipients commonly used by those skilled in the art, depending of course upon the requirements of the particular formulation.

By virtue of the novel excipient of the present invention, the amount of the novel excipient compared to the amount of microcrystalline cellulose which must be used in a wet granulation technique to obtain an acceptable solid dosage form is substantially reduced.

In other embodiments of the invention, a further material is added to the aqueous slurry of microcrystalline cellulose and compressibility augmenting. Such additional materials include silicon dioxides, non-silicon metal oxides, starches, starch derivatives, surfactants, polyalkylene oxides, cellulose ethers, celluloses esters, mixtures thereof, and the like. Specific further materials which may be included in the aqueous slurry (and consequently in the resultant agglomerated microcrystalline cellulose excipient) are aluminum oxide, stearic acid, kaolin, polydimethylsiloxane, silica gel, titanium dioxide, diatomaceous earth, corn starch, high amylose corn starch, high amylopectin corn starch, sodium starch glycolate, hydroxylated starch, modified potato starch, mixtures thereof, and the like. These additives may be included in desired amounts which will be apparent to those skilled in the art.

In addition to one or more active ingredients, additional pharmaceutically acceptable excipients (in the case of pharmaceuticals) or other additives known to those skilled in the art (for non-pharmaceutical applications) can be added to the novel excipient prior to preparation of the final product. For example, if desired, any generally accepted soluble or insoluble inert pharmaceutical filler (diluent) material can be included in the final product (e.g., a solid dosage form). Preferably, the inert pharmaceutical filler comprises a monosaccharide, a disaccharide, a polyhydric alcohol, inorganic phosphates, sulfates or carbonates, and/or mixtures thereof. Examples of suitable inert pharmaceutical fillers include sucrose, dextrose, lactose, xylitol, fructose, sorbitol, calcium phosphate, calcium sulfate, calcium carbonate, "off-the-shelf" microcrystalline cellulose, mixtures thereof, and the like.

An effective amount of any generally accepted pharmaceutical lubricant, including the calcium or magnesium soaps may optionally be added to the novel excipient at the time the medicament is added, or in any event prior to compression into a solid dosage form. The lubricant may comprise, for example, magnesium stearate in any amount of about 0.5–3% by weight of the solid dosage form. In embodiments where a surfactant is included as part or all of the compressibility augmenting agent, an additional inclusion lubricant may not be necessary.

The complete mixture, in an amount sufficient to make a uniform batch of tablets, may then subjected to tableting in a conventional production scale tableting machine at normal compression pressures for that machine, e.g., about 1500–10,000 lbs/sq in. The mixture should not be compressed to such a degree that there is subsequent difficulty in its hydration when exposed to gastric fluid.

The average tablet size for round tablets is preferably about 50 mg to 500 mg and for capsule-shaped tablets about 200 mg to 2000 mg. However, other formulations prepared in accordance with the present invention may be suitably shaped for other uses or locations, such as other body cavities, e.g., periodontal pockets, surgical wounds, vaginally. It is contemplated that for certain uses, e.g., antacid tablets, vaginal tablets and possibly implants, that the tablet will be larger.

The active agent(s) which may be incorporated with the novel excipient described herein into solid dosage forms invention include systemically active therapeutic agents, locally active therapeutic agents, disinfecting agents, chemical impregnants, cleansing agents, deodorants, fragrances, dyes, animal repellents, insect repellents, fertilizing agents, pesticides, herbicides, fungicides, and plant growth stimulants, and the like.

A wide variety of therapeutically active agents can be used in conjunction with the present invention. The therapeutically active agents (e.g. pharmaceutical agents) which may be used in the compositions of the present invention include both water soluble and water insoluble drugs. Examples of such therapeutically active agents include antihistamines (e.g., dimenhydrinate, diphenhydramine, chlorpheniramine and dexchlorpheniramine maleate), analgesics (e.g., aspirin, codeine, morphine, dihydromorphone, oxycodone, etc.), non-steroidal anti-inflammatory agents (e.g., naproxyn, diclofenac, indomethacin, ibuprofen, sulindac), anti-emetics (e.g., metoclopramide), antiepileptics (e.g., phenytoin, meprobamate and nitrazepam), vasodilators (e.g., nifedipine, papaverine, diltiazem and nicardirine), anti-tussive agents and expectorants (e.g., codeine phosphate), anti-asthmatics (e.g. theophylline), antacids, anti-spasmodics (e.g. atropine, scopolamine), antidiabetics (e.g., insulin), diuretics (e.g., ethacrynic acid, bendrofluazide), anti-hypotensives (e.g., propranolol, clonidine), antihypertensives (e.g., clonidine, methyldopa), bronchodilators (e.g., albuterol), steroids (e.g., hydrocortisone, triamcinolone, prednisone), antibiotics (e.g., tetracycline), antihemorrhoidals, hypnotics, psychotropics, antidiarrheals, mucolytics, sedatives, decongestants, laxatives, vitamins, stimulants (including appetite suppressants such as phenylpropanolamine). The above list is not meant to be exclusive.

A wide variety of locally active agents can be used in conjunction with the novel excipient described herein, and include both water soluble and water insoluble agents. The locally active agent(s) which may be included in the controlled release formulation of the present invention is intended to exert its effect in the environment of use, e.g., the oral cavity, although in some instances the active agent may also have systemic activity via absorption into the blood via the surrounding mucosa.

The locally active agent(s) include antifungal agents (e.g., amphotericin B, clotrimazole, nystatin, ketoconazole, miconazol, etc.), antibiotic agents (penicillins, cephalosporins, erythromycin, tetracycline, aminoglycosides, etc.), antiviral agents (e.g, acyclovir, idoxuridine, etc.), breath fresheners (e.g. chlorophyll), anti-tussive agents (e.g., dextromethorphan hydrochloride), anti-cariogenic compounds (e.g., metallic salts of fluoride, sodium monofluorophosphate, stannous fluoride, amine fluorides), analgesic agents (e.g., methylsalicylate, salicylic acid, etc.), local anesthetics (e.g., benzocaine), oral antiseptics (e.g., chlorhexidine and salts thereof, hexylresorcinol, dequalinium chloride, cetylpyridinium chloride), anti-inflammatory agents (e.g., dexamethasone, betamethasone, prednisone, prednisolone, triamcinolone, hydrocortisone, etc.), hormonal agents (oestriol), antiplaque agents (e.g, chlorhexidine and salts thereof, octenidine, and mixtures of thymol, menthol, methysalicylate, eucalyptol), acidity reducing agents (e.g., buffering agents such as potassium phosphate dibasic, calcium carbonate, sodium bicarbonate, sodium and potassium hydroxide, etc.), and tooth desensitizers (e.g., potassium nitrate). This list is not meant to be exclusive. The solid formulations of the invention may also include other locally active agents, such as flavorants and sweeteners. Generally any flavoring or food additive such as those described in *Chemicals Used in Food Processing*, pub 1274 by the National Academy of Sciences, pages 63–258 may be used. Generally, the final product may include from about 0.1% to about 5% by weight flavorant.

The tablets of the present invention may also contain effective amounts of coloring agents, (e.g., titanium dioxide, F.D. & C. and D. & C. dyes; see the Kirk-Othmer Encyclopedia of Chemical Technology, Vol. 5, pp. 857–884, hereby incorporated by reference), stabilizers, binders, odor controlling agents, and preservatives.

Alternatively, the novel excipient can be utilized in other applications wherein it is not compressed. For example, the granulate can be admixed with an active ingredient and the mixture then filled into capsules. The granulate can further be molded into shapes other than those typically associated with tablets. For example, the granulate together with active ingredient can be molded to "fit" into a particular area in an environment of use (e.g., an implant). All such uses would be contemplated by those skilled in the art and are deemed to be encompassed within the scope of the appended claims.

In further embodiments of the invention, more than one compressibility augmenting agent is used. Thus, for example, it is possible to use two or more agents which act as physical barriers (e.g., physically restricting the proximity of the interface between adjacent cellulose surfaces); or to use two or more agents which inhibit interactions between adjacent cellulose surfaces, for example, via the creation of a hydrophobic boundary at cellulose surfaces (e.g., surfactants having the requisite HLB value, and/or highly polar materials such as the previously mentioned dyes).

In certain preferred embodiments, two or more compressibility enhancing agents are used which provide an effect by different mechanisms, such as one agent which acts as a physical barrier (such as colloidal silicon dioxide), and another agent which inhibit interactions between adjacent cellulose surfaces (for example, sodium lauryl sulfate). In such embodiments, it is preferred that both agents are incorporated into the aqueous slurry and dried (e.g., via spray drying) to form agglomerated particles in which the microcrystalline cellulose, colloidal silicon dioxide and sodium lauryl sulfate are in intimate association. Such preferred embodiments are capable of providing a synergistically improved microcrystalline cellulose excipient which has properties described above which are at least as good, and preferably improved, as compared to the properties of the novel microcrystalline cellulose excipients which include only one class of these compressibility augmenting agents.

DETAILED DESCRIPTION OF THE PREFERRED EMBODIMENTS

The following examples illustrate various aspects of the present invention. They are not to be construed to limit the claims in any manner whatsoever.

The examples set forth the preparation of various microcrystalline cellulose/silicon dioxide compositions. Tablets were prepared using each of the compositions and each of tablet preparations was tested for tensile strength.

Examples 1–3

Preparation of Coprocessed Microcrystalline Cellulose-SiO$_2$ Compositions and Granulations Thereof Example 1

MCC-SiO$_2$ Product-5% w/w SiO$_2$

A. EXCIPIENT PARTICLES

In this example, about 6.2 kilograms of microcrystalline cellulose (MCC), (Mendell Co., Inc. Patterson, N.Y.) in the form of a wet cake was combined with 5.2 kilograms of water in a mix tank to form a slurry containing about 15% solids. The pH was adjusted to about neutral with about 3 ml of ammonium hydroxide. The slurry was allowed to mix for about 15 minutes before being combined with 5% w/w silicon dioxide (SiO$_2$), 200 m$^2$/g (CaboSil, PTG grade, available from Cabot Corp., Tuscola, Ill.) After allowing the materials to become intimately combined, the slurry was spray dried using a Niro Production Minor (Niro, Columbia, Md.), inlet temperature-215° C., outlet temperature-125° C., atomizer wheel speed 22,300 rpm, to provide microcrystalline cellulose-SiO$_2$ having an average particle size of 40–60 microns.

B. GRANULATION OF EXCIPIENT PARTICLES

The microcrystalline cellulose-SiO$_2$ particles obtained as a result of step 1 A. were wet granulated in a Baker-Perkins 10 liter high-sheer granulator for 3 minutes using water as the granulating fluid. The resultant product was wet screened through a 12 mesh screen, tray dried in a convection oven for about 2–3 hours until a moisture content of less than 5% was obtained, dry screened and sieved to obtain an average particle size of from about 55 to about 70 microns.

Example 2

MCC-SiO$_2$ Product-20% w/w SiO$_2$

The processes of Example 1A and B were repeated except that 20% w/w silicon dioxide was used to form the product.

Example 3

MCC-SiO$_2$ Product-2% w/w SiO$_2$

In this example, the processes of Example 1A and B were repeated except that 2% w/w silicon dioxide was used to form the product.

Example 4

Dry Blend Mix of MCC and SiO$_2$ (5% w/w)-Comparative

As a control, EMCOCEL® grade 50 M microcrystalline cellulose (Mendell Co., Inc.) and 5% w/w silicon dioxide, 200 m$^2$/g (CaboSil, PTG grade) were dry blended. No spray drying or other treatment of the mixture was undertaken. The method of Example 1B, however, was repeated.

Example 5

Processed MCC without SiO2

As a second control, the process described in Example 1B was repeated except that no SiO$_2$ was added.

Example 6

In this example, batches of compressed tablets were prepared using each of the products obtained as a result of Examples 1–5. The tablets were prepared using a Korsch tablet press having a punch size of ⅜" and an aim weight of about 245 mg. The granulations were included in five separate tabletting runs using compression forces of 6, 12, 18, 24 and 30 kN respectively. Ten tablets from each run were weighed, measured for diameter and tested for thickness and hardness on the Erweka TBH 30 tablet hardness tester to determine the compressibility of the microcrystalline cellulose as measured by tensile strength. The results of the analysis are graphically illustrated in FIG. 1 as a comparison of tensile strength versus compression force.

As can be seen from the graph, substantial benefits are obtained by coprocessing microcrystalline cellulose with SiO$_2$. The tablets prepared using the products of comparative examples 4 and 5 demonstrated poor tensile strength. The novel excipient is superior and demonstrates approximately the same relative improvement across the entire range of compression forces. Furthermore, the graph also illustrates that tablets prepared with a mere dry admixture of microcrystalline cellulose and SiO$_2$ (example 4 formulation) failed to demonstrate acceptable tensile strengths. Thus, the coprocessed microcrystalline cellulose-SiO$_2$ described herein provides significant retention of microcrystalline cellulose compressibility.

Examples 7–12

In these examples, compressed tablet products containing 70% by weight microcrystalline cellulose and 30% acetaminophen (APAP herein) were prepared. The products of examples 7–9 were controls and prepared without the coprocessed microcrystalline cellulose-SiO$_2$ of the present invention. The products of examples 10–12, on the other hand, included 70% by weight of the novel coprocessed microcrystalline cellulose-SiO$_2$ and 30% APAP. Details concerning the preparation of each granulation product is set forth below. A graphical comparison of the tensile strength versus compression force for each tabletted product is provided in FIG. 2.

Example 7

Intragranulation and Extragranulation of APAP with Microcrystalline Cellulose

In this example, tablets were prepared using off-the-shelf microcrystalline cellulose (EMCOCEL® 50 M) according to the following formula:

| INGREDIENTS | WEIGHT (GRAMS) |
|---|---|
| Microcrystalline cellulose | 267.9 |
| APAP | 114.8 |
| Deionized water | 165.8 |

One half of the microcrystalline cellulose was added to a Baker-Perkins 10 liter blender and combined with all of the APAP. The blender impeller was adjusted to 200 rpm and the chopper was set at 1000 rpm. After one minute, the water was added over 90 seconds using a rinse bottle. Thereafter, mixing was continued for an additional 90 seconds. The granulation was removed from the blender, wet screened through a 12 screen mesh and dried in a convection oven for 2–3 hours at 60° C. until a moisture content of less than 5% was obtained. The granulation was then dry screened through a 16 mesh screen before being blended for 10 minutes with the remaining portion of the microcrystalline cellulose in a two quart V-blender. The granulation was removed from the blender and tabletted in accordance with the method described below.

Tablet Strength Testing

In order to prepare tablets for the formulations of examples 7, 8, 10 and 11, the following procedure was used:

the wet granulation products were weighed and mixed in a 2 quart V-blender for 5 minutes with 0.2% Pruv™ (sodium stearyl fumarate, available from Mendell Co., Inc.).

Five separate tabletting runs were undertaken with compression forces of 5, 10, 15, 20 and 25 kN respectively using a Korsch tablet press having a punch size of ⅜" and an aim weight of about 245 mg. Ten tablets from each compression force were selected and used in the experiment set forth in Example 13.

Example 8

Wet Granulation of APAP With MCC

In this example, only wet granulation or the intragranulation step as described above was undertaken. The formulation was prepared according to the following formula using off-the-shelf EMCOCEL® 50 M microcrystalline cellulose:

| INGREDIENTS | WEIGHT (GRAMS) |
|---|---|
| Microcrystalline cellulose | 178.6 |
| APAP | 76.5 |
| Deionized water | 170.1 |

The microcrystalline cellulose was added to a Baker-Perkins 10 liter blender and combined with the APAP. The blender impeller was adjusted to 200 rpm and the chopper was set at 1000 rpm. After one minute, the water was added over 90 seconds using a rinse bottle. Thereafter, mixing was continued for an additional 90 seconds. The granulation was removed from the blender, wet screened through a 12 screen mesh and then dried in a convection oven at 60° C. for 2–3 hours, until a moisture content of less than 5% was achieved. The granulation was then dry screened through a 16 mesh screen and tabletted in accordance with the method described in example 7.

Example 9

Direct Compression Formulation of APAP With MCC

A direct compression formulation for tablets was prepared to contain 70% off-the-shelf EMCOCEL® 50 M microcrystalline cellulose and 30% APAP by weight. The tablets were prepared according to the following formula:

| INGREDIENTS | WEIGHT (GRAMS) |
|---|---|
| Microcrystalline cellulose | 175.0 |
| APAP | 74.5 |
| PRUV | 0.5 |

The microcrystalline cellulose and APAP were combined in a V-blender and mixed for 15 minutes. Thereafter, the Pruv® (stearyl fumarate, commercially available from Edward Mendell Co., Inc.) was added and mixing was continued for another 5 minutes. The granulation was removed and five separate tabletting runs were undertaken using compression forces of 5, 10, 15, 20 and 25 kN respectively on a Korsch tablet press. The tablet press had a punch size of ⅜" and an aim weight of about 245 mg. Ten tablets from each compression force were used in the experiment set forth in Example 13.

Example 10

Wet Granulation of APAP With Coprocessed Microcrystalline Cellulose-SiO$_2$ (5% w/w)

In this example, tablets were prepared by wet granulation with the coprocessed microcrystalline cellulose (5% w/w SiO$_2$) of Example 1A. The tablet granulation was prepared according to the following formula:

| INGREDIENTS | WEIGHT (GRAMS) |
|---|---|
| Microcrystalline Cellulose-SiO$_2$ | 178.6 |
| APAP | 76.5 |
| Deionized water | 170.1 |

The microcrystalline cellulose-SiO$_2$ was added to a Baker-Perkins 10 liter blender and combined with the APAP. The blender impeller was adjusted to 200 rpm and the chopper was set at 1000 rpm. After one minute, the water was added over 90 seconds using a rinse bottle. Thereafter, mixing was continued for an additional 90 seconds. The granulation was removed from the blender, wet screened through a 12 screen mesh and then dried in a convection oven for 2–3 hours at 60° C. until a moisture content of less than 5% was achieved. The granulation was then dry screened through a 16 mesh screen and tabletted according to the method set forth in Example 7.

Example 11

Intra- and Extragranulation of APAP with Microcrystalline Cellulose-SiO$_2$ (5% w/w)

| INGREDIENTS | WEIGHT (GRAMS) |
|---|---|
| Microcrystalline Cellulose-SiO$_2$ | 267.9 |
| APAP | 114.8 |
| Deionized water | 165.8 |

One half of the coprocessed Microcrystalline cellulose-SiO$_2$ (prepared as in Example 1A) was added to a Baker-Perkins 10 liter blender and combined with all of the APAP. The blender impeller was adjusted to 200 rpm and the chopper was set at 1000 rpm. After one minute, the water was added over 90 seconds using a rinse bottle. Thereafter, mixing was continued for an additional 90 seconds. The granulation was removed from the blender, wet screened through a 12 screen mesh and then dried in a convection oven for 2–3 hours at 60° C. until a moisture content of less than 5% was achieved. The granulation was then dry screened through a 16 mesh screen before being blended for 10 minutes with the remaining portion of the coprocessed Microcrystalline cellulose-SiO$_2$ in a 2 quart V-blender, removed from the blender, and tabletted according to the method of Example 7.

Example 12

Direct Compression Formulation of APAP With Microcrystalline Cellulose-SiO$_2$ (5% w/w)

A direct compression formulation similar to that set forth in example 9 was undertaken except that the tablets were prepared to contain the coprocessed Microcrystalline cellulose-SiO$_2$ of Example 1A. The tablet granulation was prepared according to the following formula:

| INGREDIENTS | WEIGHT (GRAMS) |
|---|---|
| Microcrystalline cellulose-SiO$_2$ | 175.0 |
| APAP | 74.5 |
| PRUV | 0.5 |

As was the case in example 9, five separate tabletting runs were undertaken using compression forces of 5, 10, 15, 20 and 25 kN respectively on a Korsch tablet press, (punch size: ⅜" and aim weight—about 245 mg). Ten tablets from each compression force were used to carry out the experiment set forth in Example 13.

Example 13

Tablet Strength Testing

Ten tablets from each compression force run for each formulation prepared in Examples 7–12 were weighed, measured for diameter and tested for thickness and hardness on the Erweka TBH 30 tablet hardness tester to determine the compressibility of the microcrystalline cellulose. The results are graphically illustrated in FIG. 2 as a comparison of tensile strength versus compression force.

Figure 2:
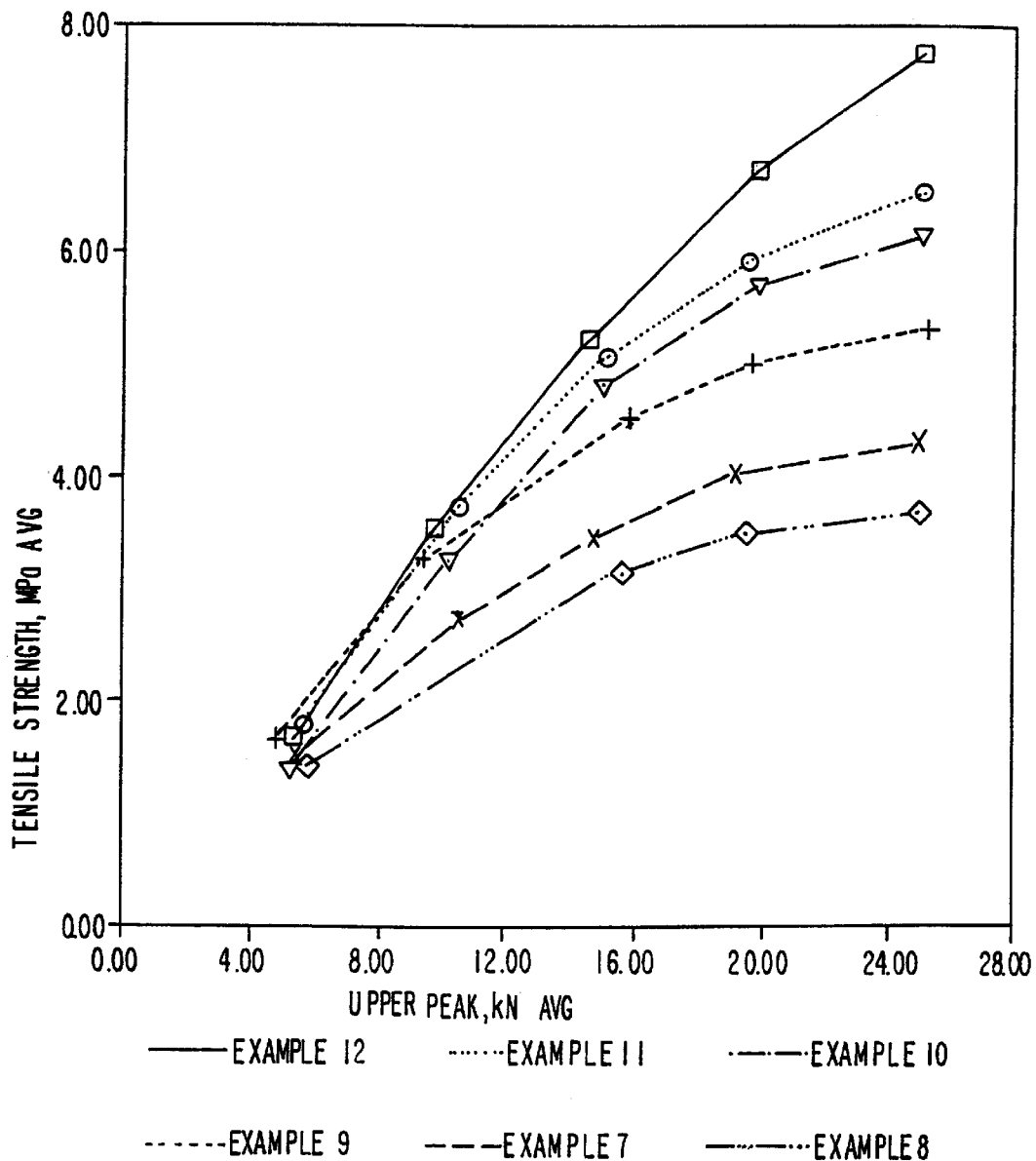
FIG. 2 graphically shows a comparison of the tensile strength of APAP containing tablets prepared in accordance with the invention and prior art APAP containing tablets.

Referring now to FIG. 2, it can be seen that compressed tablets made with the inventive coprocessed Microcrystalline cellulose-SiO$_2$ have relatively high tensile strengths when compared to those made with off-the-shelf Microcrystalline cellulose. The advantages of the coprocessed Microcrystalline cellulose-SiO$_2$ are clearly seen in both direct compression and wet granulation formulations and especially in wet granulation products.

Examples 14–16

Diatomaceous Earth

In these examples, the coprocessing method described in Example 1A was repeated except that diatomaceous earth of about 40 micron particle size (J. T. Baker, Phillipsburg, N.J. was used as the source of SiO$_2$).

| Example | Diatomaceous Earth (wt %) |
|---|---|
| 14 | 2.0 |
| 15 | 1.0 |
| 16 | 0.5 |

The resultant granulates prepared according to Example 1B were tabletted according to the same method described in Example 6 and evaluated for tensile strength. The products of inventive Example 3 (Microcrystalline cellulose-SiO$_2$ 2% w/w) and Example 5 (Microcrystalline cellulose alone) were included in FIG. 3 for comparison purposes.

Figure 3:
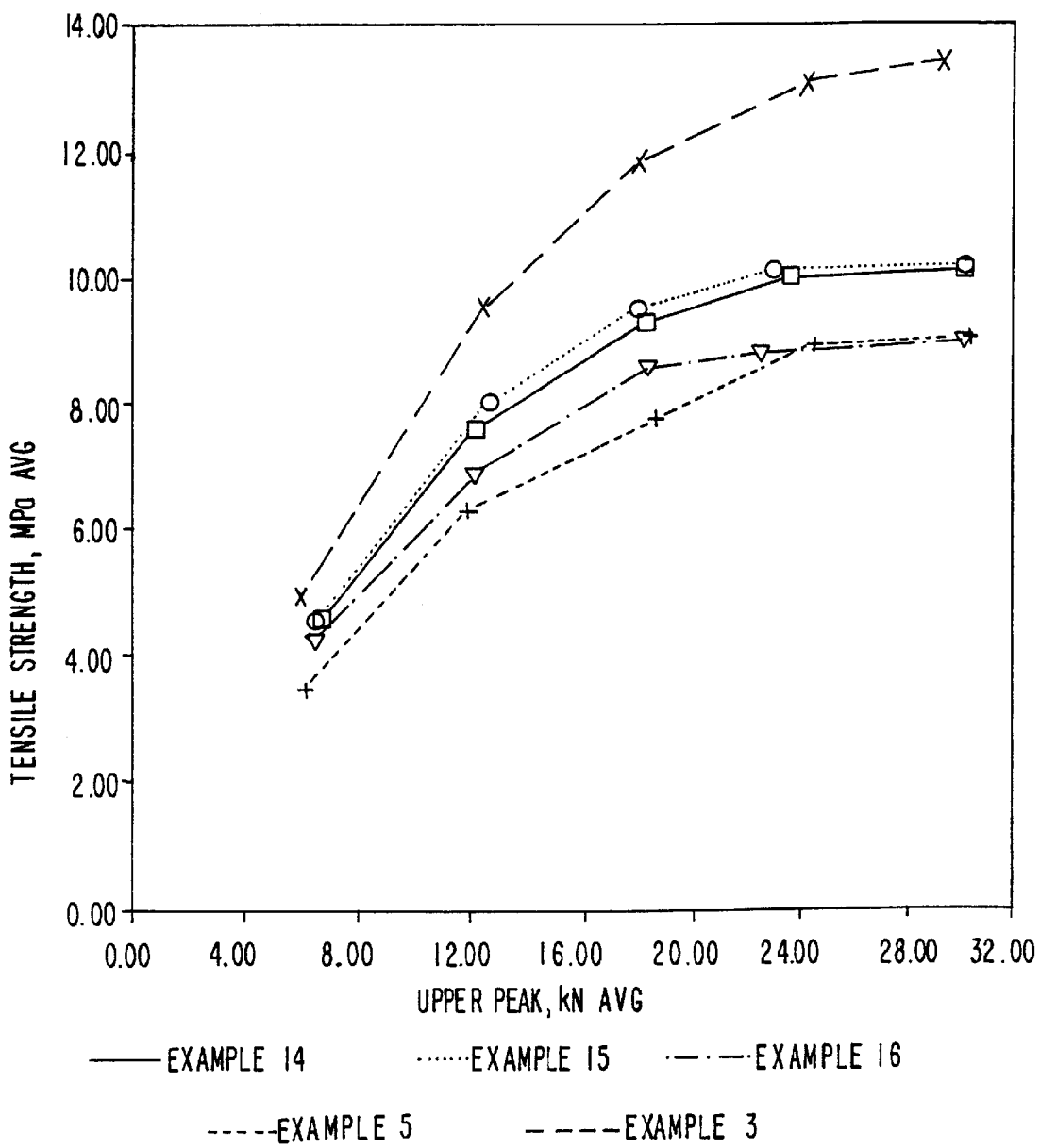
FIG. 3 graphically shows a comparison of the tensile strength of tablets prepared in accordance with the invention to contain microcrystalline cellulose coprocessed with diatomaceous earth, tablets containing microcrystalline cellulose coprocessed with 2% w/w $SiO_2$ and prior art tablets prepared to contain only unmodified microcrystalline cellulose.

Referring now to FIG. 3, it can be seen that although the retention of compressibility afforded by coprocessing diatomaceous earth is not as great as that provided by colloidal SiO$_2$ having surface areas of about 200 m$^2$/g, the coprocessed Microcrystalline cellulose-diatomaceous earth nonetheless demonstrates improved compressibility in wet granulation formulations.

Examples 17–19

Silica Gel SILICA GEL

In these examples, the coprocessing method described in Example 1A was repeated using silica gel 200 micron particle size (VWR Corp., Piscataway, N.J. as the source of SiO$_2$).

| Example | Silica Gel (wt %) |
|---------|-------------------|
| 17      | 1                 |
| 18      | 2                 |
| 19      | 5                 |

The resultant granulates prepared according to Example 1B were tabletted according to the same method described in Example 6 and evaluated for tensile strength. The products of inventive Example 3 (Microcrystalline cellulose-$SiO_2$ 2% w/w) and Example 5 (Microcrystalline cellulose alone) were included in FIG. 4 for comparison purposes.

Figure 4:
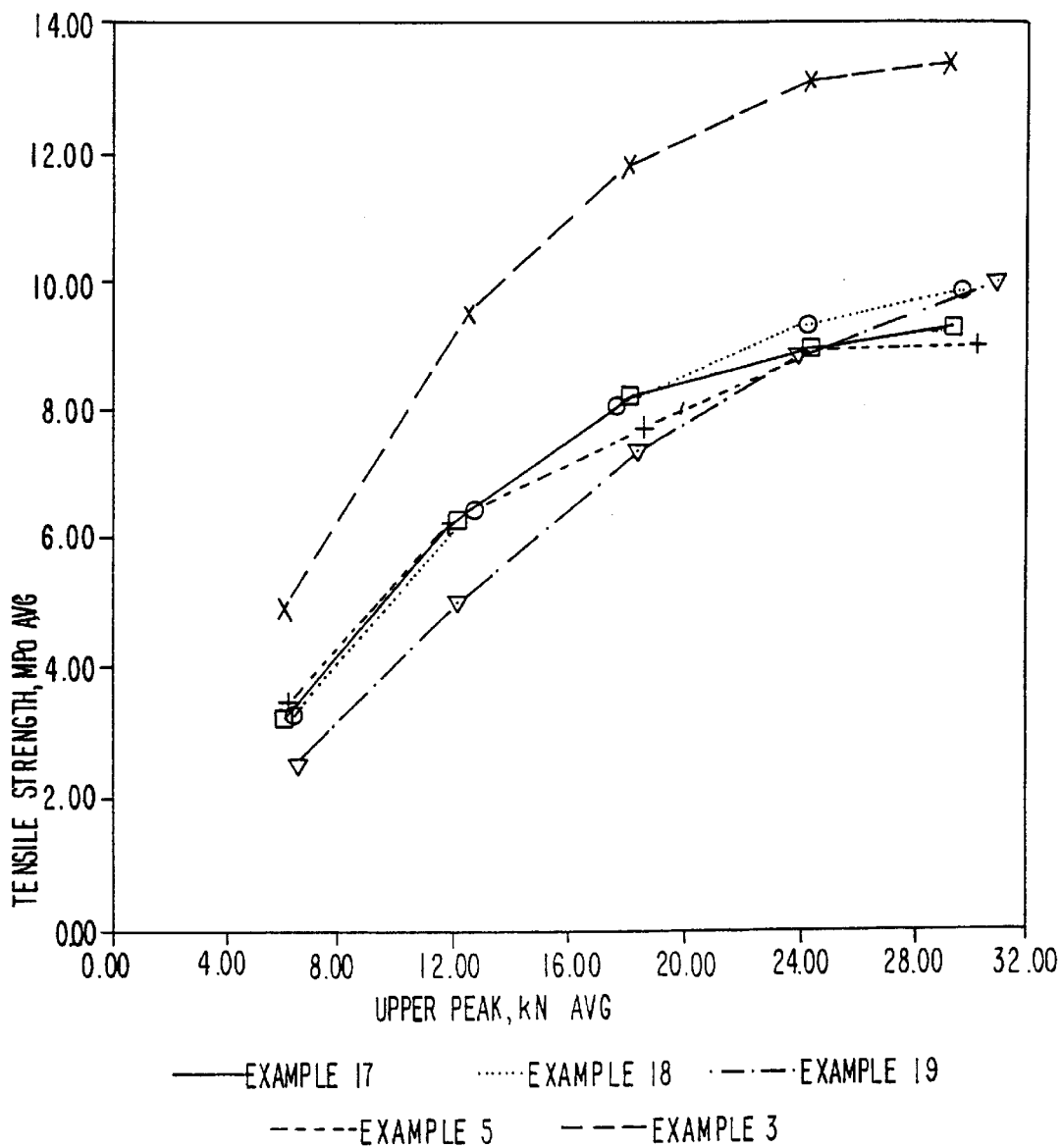
FIG. 4 graphically illustrates a comparison of the tensile strength of tablets prepared W using microcrystalline cellulose coprocessed with silica gel, tablets prepared with the novel coprocessed microcrystalline cellulose and tablets prepared with microcrystalline cellulose alone.

Referring now to FIG. 4, it can be seen that the retention of compressibility afforded by coprocessing with silica gel is well below that provided by colloidal $SiO_2$ having surface areas of about 200 $m^2$/g. In fact, Microcrystalline cellulose coprocessed with silica gel demonstrates compressibility properties about the same as off-the-shelf Microcrystalline cellulose in wet granulation formulations.

Examples 20–22

HS-5 Grade Silicon Dioxide

In these examples, the coprocessing method described in example 1 was repeated using HS-5 grade $SiO_2$ surface area—325 $m^2$/g (Cabot Corp., Tuscola, Ill.).

| Example | Silica Gel (wt %) |
|---------|-------------------|
| 20      | 2                 |
| 21      | 1                 |
| 22      | 0.5               |

The resultant granulates prepared according to Example 1B were tabletted according to the same method described in Example 6 and evaluated for tensile strength. The products of inventive Example 3 (Microcrystalline cellulose-$SiO_2$ 2% w/w) and Example 5 (off-the-shelf Microcrystalline cellulose) were included in FIG. 5 for comparison purposes.

Figure 5:
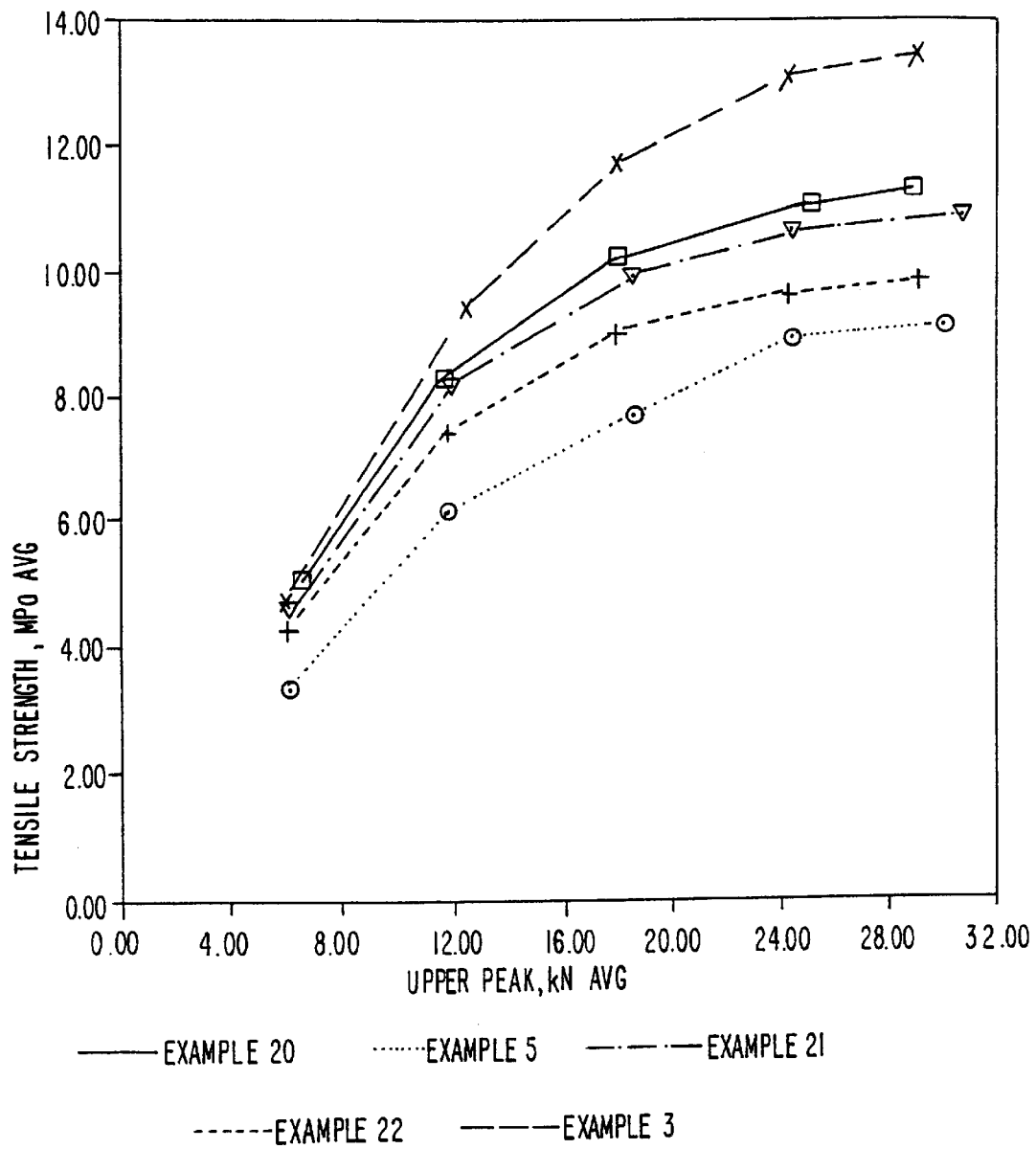
FIG. 5 graphically illustrates a comparison of the tensile strength of tablets prepared using microcrystalline cellulose coprocessed with HS 5 grade $SiO_2$, tablets prepared using coprocessed microcrystalline cellulose-$SiO_2$ and prior art tablets prepared to contain only unmodified microcrystalline cellulose.

Referring now to FIG. 5, the retention of compressibility afforded by coprocessing with HS-5 is comparable to that obtained using $SiO_2$ having surface areas of about 200 $m^2$/g.

While there have been described what are presently believed to be the preferred embodiments of the invention, those skilled in the art will realize that changes and modifications may be made thereto without departing from the spirit of the invention. It is intended to claim all such changes and modifications that fall within the true scope of the invention.

Examples 23–25

Preparation of Coprocessed Microcrystalline Cellulose-SLS Compositions and Granulations Thereof Example 23

Microcrystalline Cellulose-SLS Product-0.25% w/w SLS

A. EXCIPIENT PARTICLES

In this example, about 6.2 kilograms of microcrystalline cellulose (Microcrystalline cellulose), (Mendell Co., Inc. Patterson, N.Y.) in the form of a wet cake was combined with 5.2 kilograms of water in a mix tank to form a slurry containing about 15% solids. The pH was adjusted to about neutral with about 3 ml of ammonium hydroxide. The slurry was allowed to mix for about 15 minutes before being combined with 0.25% w/w sodium lauryl sulfate (SLS) powder (available from Spectrum Chemical, Gardena, Calif.) After allowing the materials to become intimately combined, the slurry was spray dried using a Niro Production Minor (Niro, Columbia, Md.), inlet temperature—215° C., outlet temperature—125° C., atomizer wheel speed 22,300 rpm, to provide Microcrystalline cellulose-SLS having an average particle size of 40–60 microns.

B. GRANULATION OF EXCIPIENT PARTICLES

The Microcrystalline cellulose-SLS particles obtained as a result of step 23 A. were wet granulated in a Baker-Perkins 10 liter high-sheer granulator for 3 minutes using water as the granulating fluid. The resultant product was wet screened through a 12 mesh screen, tray dried in a convection oven for about 2–3 hours until a moisture content of less than 5% was obtained, dry screened and sieved to obtain an average particle size of from about 55 to about 70 microns.

Examples 24–27

Microcrystalline Cellulose-SLS Products

The processes of Example 23A and B were repeated except that 0.5% w/w sodium lauryl sulfate was used to form the product of Example 24; 0.1% w/w SLS was used to form the product of Example 25; 0.2% w/w SLS was used to form the product of Example 26; and 0.3% w/w SLS was used to form the product of Example 27.

Example 28

Dry Blend Mix of Microcrystalline Cellulose and SLS (0.25% w/w)-Comparative

As a control, EMCOCEL® grade 50 M microcrystalline cellulose (Mendell Co., Inc.) and 0.25% w/w SLS powder were dry blended. No spray drying or other treatment of the mixture was undertaken. The method of Example 23B, however, was repeated.

Example 29

Processed Microcrystalline Cellulose Without SLS

As a second control, the process described in Example 23B was repeated except that no SLS was added.

Example 30

Figure 6:
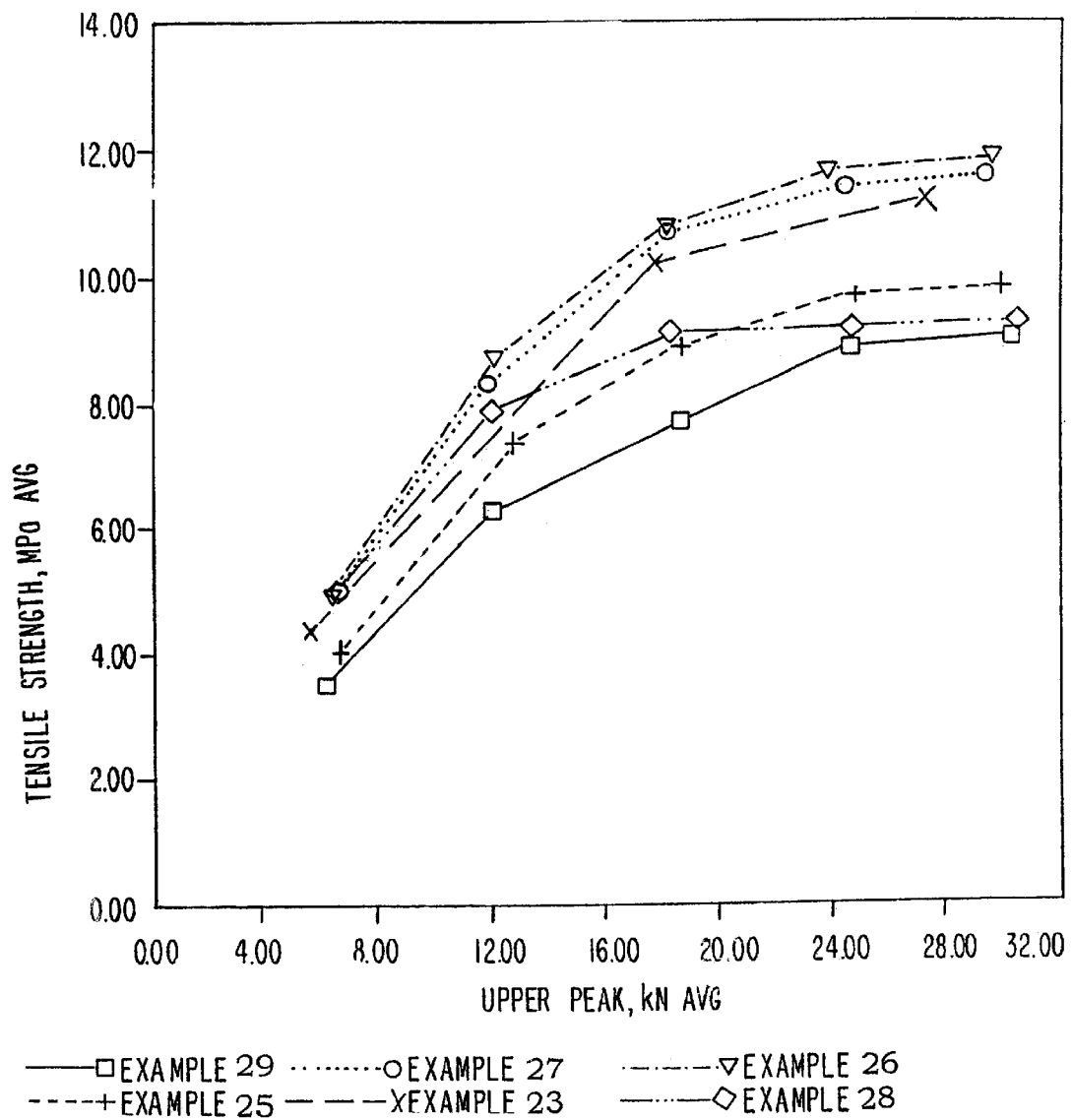
FIG. 6 graphically shows a comparison of the tensile strength of tablets prepared in accordance with the invention (compressibility augmenting agent=surfactant) and prior art tablets.

In this example, batches of compressed tablets were prepared using each of the products obtained as a result of Examples 23–29. The tablets were prepared using a Korsch tablet press having a punch size of ⅜" and an aim weight of about 245 mg. The granulations were included in five separate tabletting runs using compression forces of 6, 12, 18, 24 and 30 kN respectively. Ten tablets from each run were weighed, measured for diameter and tested for thickness and hardness on the Erweka TBH 30 tablet hardness tester to determine the compressibility of the microcrystalline cellulose as measured by tensile strength. The results of the analysis for the products of Examples 23, 25–29 are graphically illustrated in FIG. 6 as a comparison of tensile strength versus compression force. The results obtained using the product of Example 24 were determined to be comparable to that obtained for the product of Example 25 (0.1% SLS).

As can be seen from the graph, substantial benefits are obtained by coprocessing Microcrystalline cellulose with SLS. The tablets prepared using the products of comparative examples 28 and 29 demonstrated poor tensile strength. The novel excipient is superior and demonstrates approximately the same relative improvement across the entire range of compression forces. Furthermore, the graph also illustrates that tablets prepared with a mere dry admixture of Microcrystalline cellulose and SLS (Example 28 formulation) failed to demonstrate acceptable tensile strengths. Thus, the coprocessed microcrystalline cellulose-SLS described herein provides significant retention of Microcrystalline cellulose compressibility.

Examples 31–32

Docusate Sodium

In these examples, the coprocessing method described in Example 23A was repeated except that docusate sodium (Spectrum Chemical) was used as the coprocessing agent).

| Example | Docusate Sodium (wt %) |
|---|---|
| 31 | 0.25 |
| 32 | 0.50 |

The resultant granulates prepared according to Example 23B were tabletted according to the same method described in Example 30 and evaluated for tensile strength. The products of inventive Example 26 (Microcrystalline cellulose-SLS 0.20% w/w) and Example 29 (microcrystalline cellulose alone) were included in FIG. 7 for comparison purposes.

Figure 7:
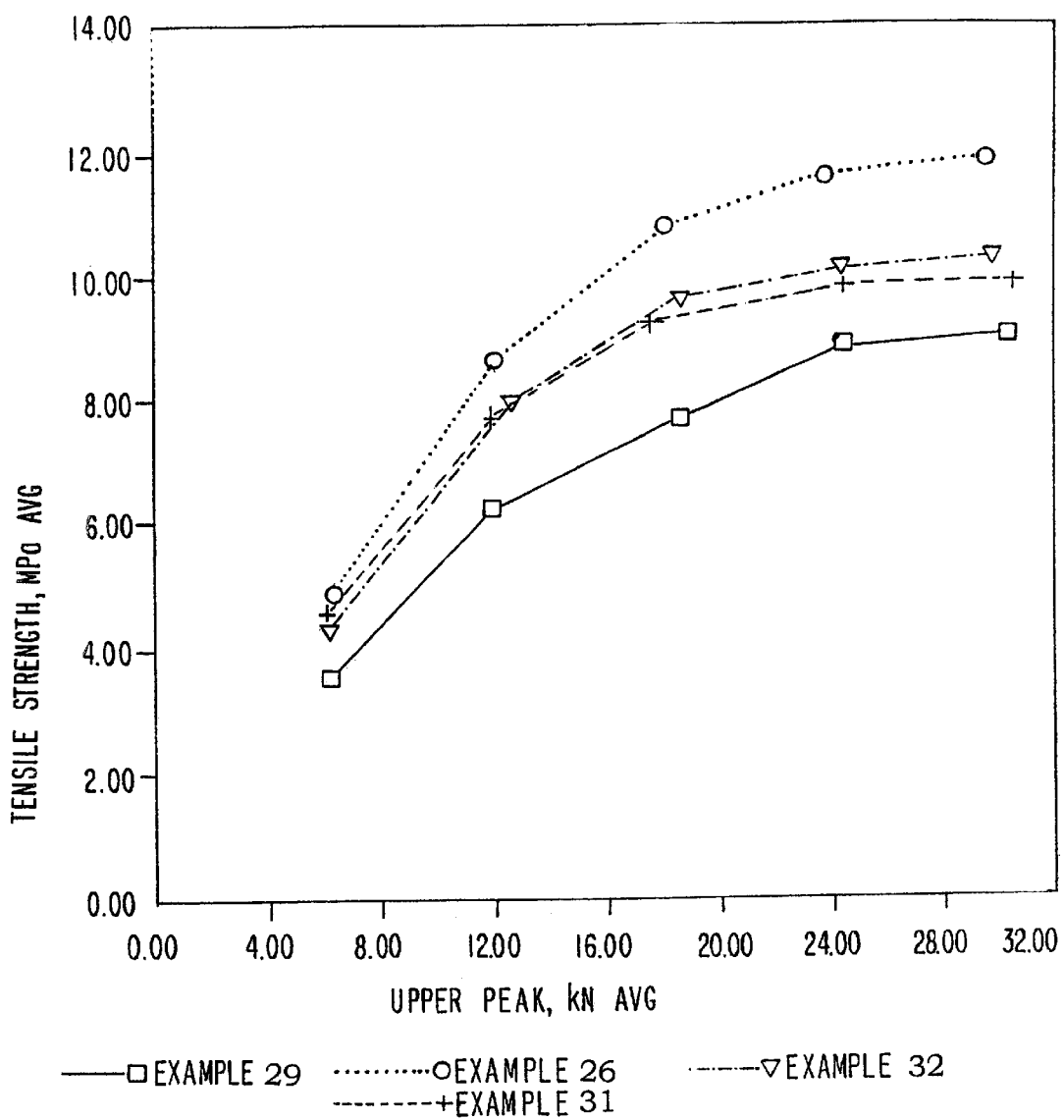
FIG. 7 graphically shows a comparison of the tensile strength of tablets prepared in accordance with the invention to contain microcrystalline cellulose coprocessed with sodium lauryl sulfate, tablets containing microcrystalline cellulose coprocessed with docusate sodium and prior art tablets prepared to contain only unmodified microcrystalline cellulose.

Referring now to FIG. 7, it can be seen that coprocessing microcrystalline cellulose with docusate sodium also affords the retention of microcrystalline cellulose compressibility.

Examples 33–36

Polysorbate 40

In these examples, the coprocessing method described in Example 23A was repeated using the non-ionic surfactant polysorbate 40 (Spectrum Chemical) as the coprocessing agent.

| Example | Polysorbate 40 (wt %) |
|---|---|
| 33 | 0.25 |
| 34 | 0.50 |
| 35 | 1.0 |
| 36 | 2.0 |

The resultant granulates prepared according to Example 23B were tabletted according to the same method described in Example 30 and evaluated for tensile strength. The products of inventive Example 26 (Microcrystalline cellulose-SLS 0.2% w/w) and Example 29 (microcrystalline cellulose alone) were included in FIG. 8 for comparison purposes.

Figure 8:
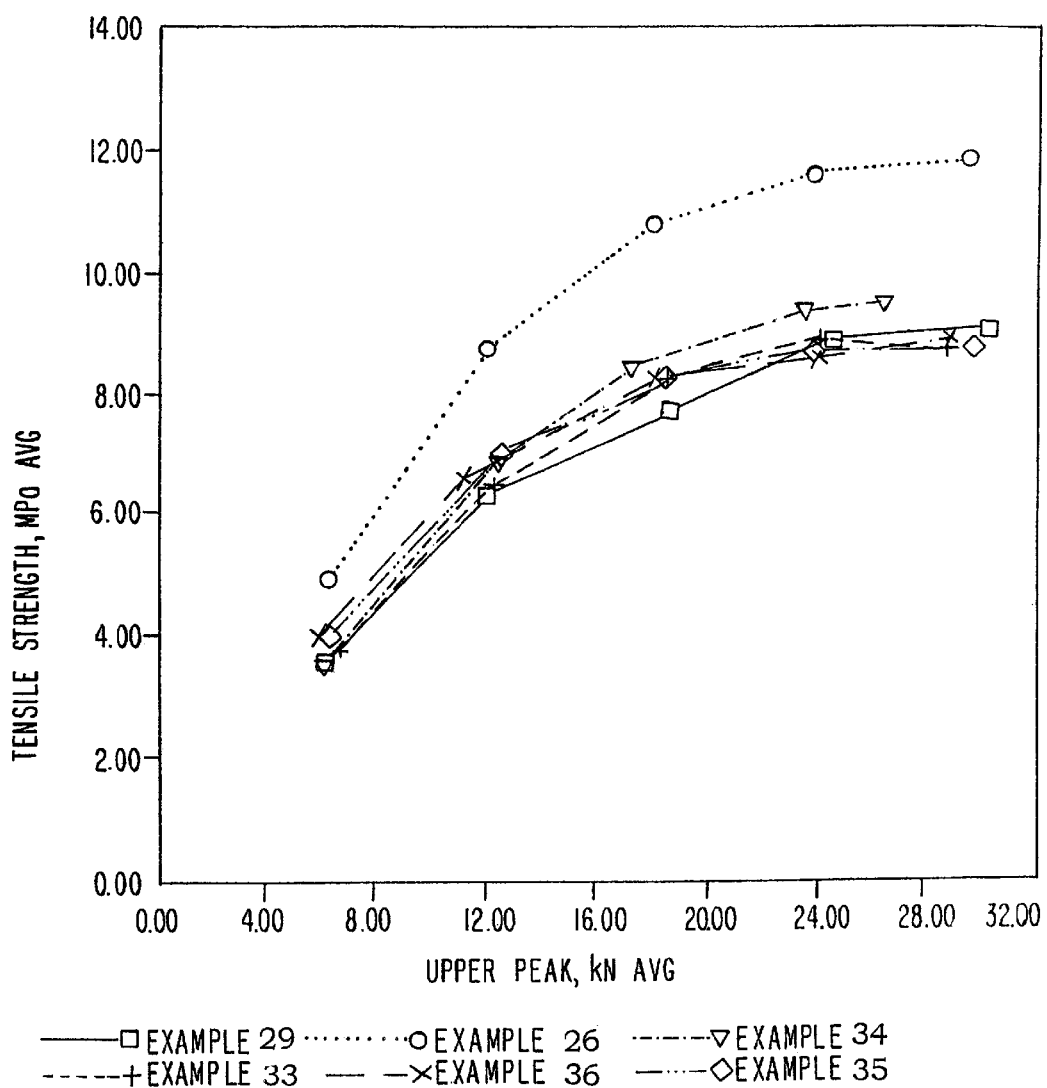
FIG. 8 graphically illustrates a comparison of the tensile strength of tablets prepared using microcrystalline cellulose coprocessed with polysorbate 40, tablets prepared with the novel sodium lauryl sulfate coprocessed microcrystalline cellulose and tablets prepared with microcrystalline cellulose alone.

Referring now to FIG. 8, it can be seen that the retention of compressibility afforded by coprocessing with polysorbate 40 is well below that provided by sodium lauryl sulfate. In fact, microcrystalline cellulose coprocessed with polysorbate 40 demonstrates compressibility properties about the same as off-the-shelf Microcrystalline cellulose in wet granulation formulations.

Examples 37–39

Simethicone

In these examples, the coprocessing method described in example 23 was repeated using simethicone (Dow Coming, Midland. Mich.) as the surfactant coprocessing agent.

| Example | Simethicone (wt %) |
|---|---|
| 37 | 0.5 |
| 38 | 1.0 |
| 39 | 2.0 |

The resultant granulates prepared according to Example 23B were tabletted according to the same method described in Example 30 and evaluated for tensile strength. The products of inventive Example 29 (Microcrystalline cellulose-SLS 0.2% w/w) and Example 29 (off-the-shelf microcrystalline cellulose) were included in FIG. 9 for comparison purposes.

Figure 9:
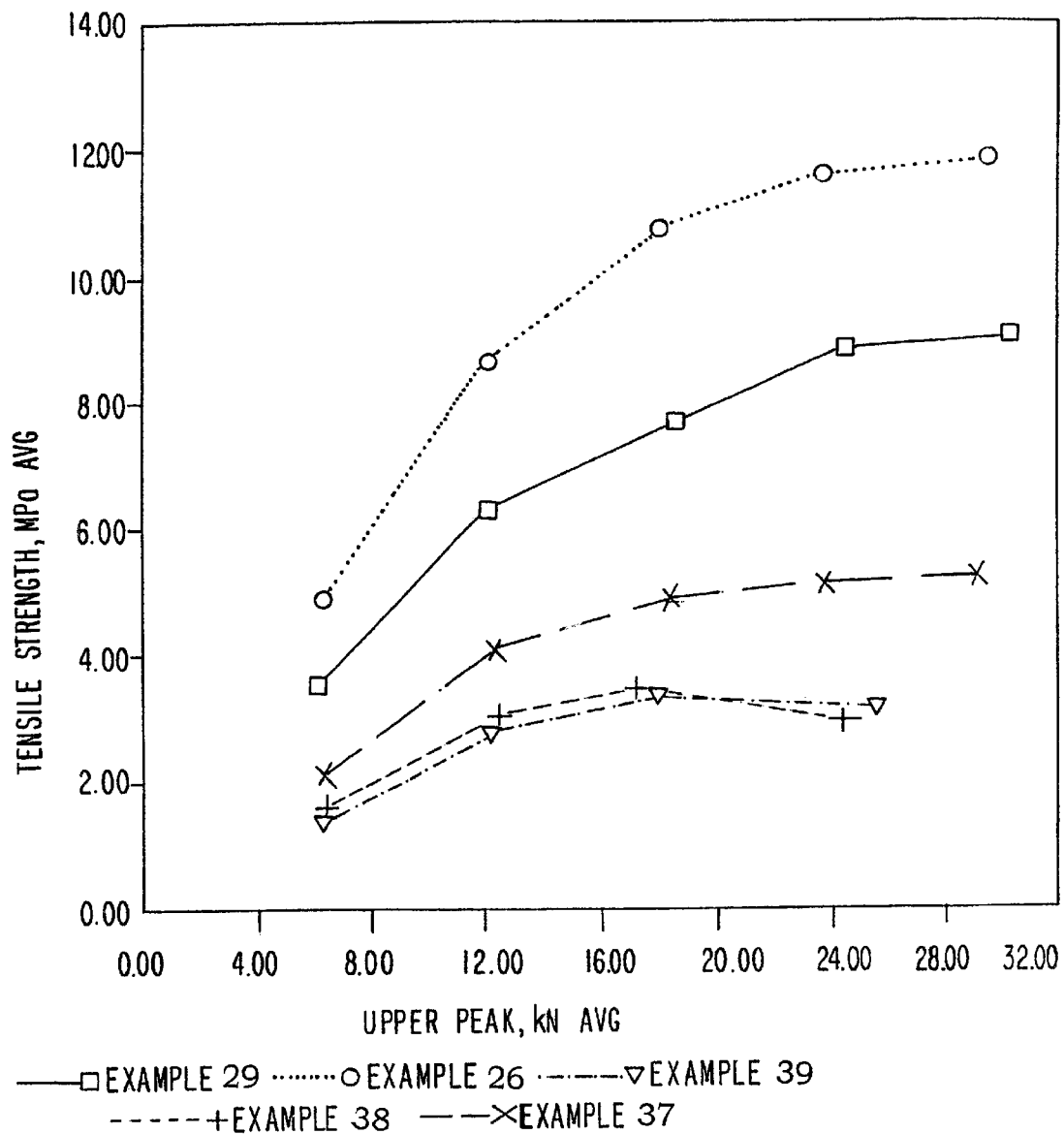
FIG. 9 graphically illustrates a comparison of the tensile strength of tablets prepared using microcrystalline cellulose coprocessed with polydimethyl siloxane (simethicone), tablets prepared using coprocessed microcrystalline cellulose-sodium lauryl sulfate and prior art tablets prepared to contain only unmodified microcrystalline cellulose.

Referring now to FIG. 9, it can be seen that this surfactant provides little, if any, improvement in the retention of microcrystalline cellulose compressibility. It can, therefore, be seen that mere addition of any lubricant in any amount is not sufficient to allow microcrystalline cellulose to retain its compressibility in wet granulations. Rather, selected surfactants, present within the claimed ranges, provide the desirable compressibility characteristics to the microcrystalline cellulose.

While there have been described what are presently believed to be the preferred embodiments of the invention, those skilled in the art will realize that changes and modifications may be made thereto without departing from the spirit of the invention. It is intended to claim all such changes and modifications that fall within the true scope of the invention.

What is claimed is:

1. A composition, comprising
microcrystalline cellulose; and
an effective amount of a compressibility augmenting agent selected from the group consisting of silicon dioxide, a surfactant, a highly polar compound, and mixtures thereof, provided that when the compressibility augmenting agent consists of said surfactant, said surfactant is present in an amount from about 0.1% to about 0.5% by weight of said microcrystalline cellulose;
said composition comprising agglomerated particles of said microcrystalline cellulose and said compressibility augmenting agent in intimate association with each other.

2. The composition of claim 1, wherein said compressibility augmenting agent provides a hydrophobic boundary at cellulose surfaces.

3. The composition of claim 1, wherein said silicon dioxide has an average primary particle size from about 1 nm to about 100 μm.

4. The composition of claim 1, wherein said silicon dioxide is colloidal silicon dioxide.

5. The composition of claim 1, wherein said surfactant has an HLB value of at least 10.

6. The composition of claim 1, wherein said surfactant has an HLB value of from about 15 to about 50.

7. The composition of claim 1, wherein said surfactant is sodium lauryl sulfate.

8. The composition of claim 1, wherein said surfactant is polysorbate 40.

9. The composition of claim 1, wherein said highly polar compound is a highly polar dye selected from the group consisting of 3,3'-[[1,1'Biphenyl]-4,4'-diylbis-(azo)]bis[4-amino-1-naphthalenesulfonic acid] disodium salt; disodium salt of 6-hydroxy-5[(2-methyl-4-sulfophenyl)azo]-2-naphthalenesulfonic acid); 5-oxo-1-(p-sulfophenyl)-4-[(p-sulfophenyl)azo]-2-pyrazoline-3-carboxylic acid, trisodium salt); disodium salt of 1-p-sulphophenylazo-2-naphthol-6-sulfonic acid); trisodium-2-hydroxy-1-(4-sulfonato-1-naphthylazo)naphthalene-6,8-disulfonate); disodium 4,4'-(2,4-dihydroxy-5-hydroxymethyl-3,3-phenylene bisazo)di (napthalene-1-sulfonate)); tetrasodium 4-acetamido-5-hyroxy-6-[7-sulfonato-4-(4-sulfonatophenylazo)-1-naphthylazo]naphthalene-1,7-disulfonate); disodium 4-hydroxy-3-(4-sulfanato-1-naphythylazo) Naphthalene-1-sulfonate); trisodium 2-hydroxy-1-(4-sulfonato-1-naphthylazo)naphthalene-3,6-disulfonate); and mixtures thereof.

10. The composition of claim 1, which is prepared in a manner which significantly reduces the hydrogen bonding between inter- and/or intra-molecular cellulose-to-cellulose bonding which occurs when microcrystalline cellulose is exposed to water.

11. The composition of claim 1, which is prepared by preparing an aqueous slurry of microcrystalline cellulose in the form of a wet cake, compressibility augmenting agent(s), and other optional ingredients, and drying the mixture in a manner which inhibits quasi-hornification.

12. The composition of claim 10, wherein the drying step is accomplished via spray drying.

13. The composition of claim 1, wherein said silicon dioxide is included in amount from about 0.1% to about 20% by weight, based on the weight of microcrystalline cellulose.

14. The composition of claim 13, wherein said silicon dioxide is included in an amount of from about 1.25% to about 5%, based on the weight of said microcrystalline cellulose.

15. The composition of claim 1, wherein said agglomerated particles have an average particle size of from about 10 μm to about 1,000 μm.

16. The composition of claim 1, wherein said agglomerated particles further comprise a member of the group consisting of non-silicon metal oxides, starches, starch derivatives, polyalkylene oxides, stearic acid, kaolin, polydimethylsiloxane, silica gel, diatomaceous earth, and mixtures thereof.

17. The composition of claim 1, wherein said silicon dioxide portion of said agglomerate is derived from a silicon dioxide having a surface area from about 10 $m^2/g$ to about 500 $m^2/g$.

18. The composition of claim 1, further comprising an active agent.

19. The composition of claim 18, wherein said agglomerated particles and said active agent are wet granulated.

20. A solid dosage form of a compressed mixture of from about 1% to about 99% of an excipient comprising a particulate agglomerate of microcrystalline cellulose and an effective amount of a compressibility augmenting agent selected from the group consisting of silicon dioxide, a surfactant, a highly polar compound, and mixtures thereof; provided that when the compressibility augmenting agent consists of said surfactant, said surfactant is present in an amount which from about 0.1% to about 0.5% by weight of said microcrystalline cellulose; and from about 99% to about 1% of a therapeutically active ingredient.

21. The composition of claim 20, which has been wet granulated prior to compression into a tablet.

22. A method of enhancing the compressibility of microcrystalline cellulose in wet granulation products, comprising:

(a) forming an aqueous slurry containing a mixture of microcrystalline cellulose in the form of a wet cake, and an effective amount of a compressibility augmenting agent to improve the compressibility of said microcrystalline cellulose, said compressibility augmenting agent selected from the group consisting of silicon dioxide, a surfactant, a highly polar compound, and mixtures thereof; and (b) drying said slurry to obtain an excipient comprising a plurality of agglomerated particles of said microcrystalline cellulose in intimate association with said compressibility enhancing agent, provided that when the compressibility augmenting agent consists of said surfactant, said surfactant is present in an amount from about 0.1% to about 0.5% by weight of said microcrystalline cellulose.

23. The method of claim 22, further comprising drying said slurry such that the resultant excipient particles have an average particle size from about 10 μm to about 1,000 μm.

24. The method of claim 22, further comprising drying said slurry such that the resultant excipient particles have a moisture content of from about 0.5 to about 15%.

25. The method of claim 22, further comprising incorporating into said slurry a member of the group consisting of non-silicon metal oxides, starches, starch derivatives, polyalkylene oxides, stearic acid, kaolin, polydimethylsiloxane, silica gel, diatomaceous earth, and mixtures thereof.

26. A method of preparing a solid dosage form, comprising:

(a) forming an aqueous slurry containing a mixture of microcrystalline cellulose in the form of a wet cake and an effective amount of a compressibility augmenting agent, said compressibility augmenting agent selected from the group consisting of silicon dioxide, a surfactant, a highly polar compound and mixtures thereof; and (b) drying said slurry to obtain an excipient comprising a plurality of agglomerated particles of said microcrystalline cellulose in intimate association with said compressibility augmenting agent;

(c) mixing an active ingredient with said excipient in a ratio from about 1:99 to about 99:1; and (d) compressing said mixture obtained in step (c) into tablets; said effective amount of the compressibility augmenting agent being sufficient to improve the compressibility of said microcrystalline cellulose, provided that when the compressibility augmenting agent consists of said surfactant, said surfactant is present in an amount from about 0.1% to about 0.5% by weight of said microcrystalline cellulose.

27. The method of claim 26, wherein said mixing in step (c) is performed via wet granulation.

28. The method of claim 22, wherein the surfactant is selected from the group consisting of polyoxyethylene compounds, lecithin, ethoxylated alcohols, ethoxylated esters, ethoxylated amides, polyoxypropylene compounds, propoxylated alcohols, ethoxylated/propoxylated block polymers, propoxylated esters, alkanolamides, amine oxides, fatty acid esters of polyhydric alcohols, ethylene glycol esters, diethylene glycol esters, propylene glycol esters, glycerol esters, polyglycerol fatty acid esters, SPAN's, sucrose esters, glucose (dextrose) esters, acacia, benzalkonium chloride, cholesterol, emulsifying wax, glycerol monostearate, lanolin alcohols, lecithin, poloxamer, polyoxyethylene, and castor oil derivatives.

29. The method of claim 22, wherein the surfactant is sodium lauryl sulfate.

30. The method of claim 22, wherein the wherein the highly polar compound is selected from the group consisting of 3,3'-[[1,1'Biphenyl]-4,4'-diylbis-(azo)]bis[4-amino-1-naphthalenesulfonic acid] disodium salt; disodium salt of 6-hydroxy-5[(2-methyl-4-sulfophenyl)azo]-2-naphthalenesulfonic acid); 5-oxo-1-(p-sulfophenyl)-4-[(p-sulfophenyl)azo]-2-pyrazoline-3-carboxylic acid, trisodium salt); disodium salt of 1-p-sulphophenylazo-2-naphthol-6-sulfonic acid); trisodium-2-hydroxy-1-(4-sulfonato-1-naphthylazo)naphthalene-6,8-disulfonate); disodium 4,4'-(2,4-dihydroxy-5-hydroxymethyl-3,3-phenylene bisazo)di(napthalene-1-sulfonate)); tetrasodium 4-acetamido-5-hyroxy-6-[7-sulfonato-4-(4-sulfonatophenylazo)-1-naphthylazo]naphthalene-1,7-disulfonate); disodium 4-hydroxy-3-(4-sulfanato-1-naphythylazo) Naphthalene-1-sulfonate); trisodium 2-hydroxy-1-(4-sulfonato-1-naphthylazo)naphthalene-3,6-disulfonate); and mixtures thereof.

31. The method of claim 26, wherein the surfacant is selected from the group consisting of polyoxyethylene compounds, lecithin, ethoxylated alcohols, ethoxylated esters, ethoxylated amides, polyoxypropylene compounds, propoxylated alcohols, ethoxylated/propoxylated block polymers, propoxylated esters, alkanolamides, amine oxides, fatty acid esters of polyhydric alcohols, ethylene glycol esters, diethylene glycol esters, propylene glycol esters, glycerol esters, polyglycerol fatty acid esters, SPAN's, sucrose esters, glucose (dextrose) esters, acacia, benzalkonium chloride, cholesterol, emulsifying wax, glycerol. monostearate, lanolin alcohols, lecithin, poloxamer, polyoxyethylene, and castor oil derivatives.

32. The method of claim 26, wherein the surfactant is sodium lauryl sulfate.

33. The method of claim 26, wherein the highly polar compound is selected from the group consisting of 3,3'-[[1,1'Biphenyl]-4,4'-diylbis-(azo)]bis[4-amino-1-naphthalenesulfonic acid] disodium salt; disodium salt of 6-hydroxy-5[(2-methyl-4-sulfophenyl)azo]-2-naphthalenesulfonic acid); 5-oxo-1-(p-sulfophenyl)-4-[(p-sulfophenyl)azo]-2-pyrazoline-3-carboxylic acid, trisodium salt); disodium salt of 1-p-sulphophenylazo-2-naphthol-6-sulfonic acid); trisodium-2-hydroxy-1-(4-sulfonato-1-naphthylazo)naphthalene-6,8-disulfonate); disodium 4,4'-(2,4-dihydroxy-5-hydroxymethyl-3,3-phenylene bisazo)di(napthalene-1-sulfonate)); tetrasodium 4-acetamido-5-hyroxy-6-[7-sulfonato-4-(4-sulfonatophenylazo)-1-naphthylazo]naphthalene-1,7-disulfonate); disodium 4-hydroxy-3-(4-sulfanato-1-naphythylazo) Naphthalene-1-sulfonate); trisodium 2-hydroxy-1-(4-sulfonato-1-naphthylazo)naphthalene-3,6-disulfonate); and mixtures thereof.

* * * * *